(12) United States Patent
Ikeda

(10) Patent No.: US 12,290,814 B2
(45) Date of Patent: May 6, 2025

(54) BUBBLE DISCHARGING METHOD, PARTICLE TRAPPING APPARATUS, AND PARTICLE ANALYZING APPARATUS

(71) Applicant: SONY GROUP CORPORATION, Tokyo (JP)

(72) Inventor: Kenji Ikeda, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 882 days.

(21) Appl. No.: 17/424,258

(22) PCT Filed: Dec. 4, 2019

(86) PCT No.: PCT/JP2019/047523
§ 371 (c)(1),
(2) Date: Jul. 20, 2021

(87) PCT Pub. No.: WO2020/158183
PCT Pub. Date: Aug. 6, 2020

(65) Prior Publication Data
US 2022/0111382 A1    Apr. 14, 2022

(30) Foreign Application Priority Data
Jan. 28, 2019  (JP) ................. 2019-011785

(51) Int. Cl.
*G01N 37/00* (2006.01)
*B01L 3/00* (2006.01)

(52) U.S. Cl.
CPC ... *B01L 3/502738* (2013.01); *B01L 3/502715* (2013.01); *B01L 2200/0673* (2013.01);
(Continued)

(58) Field of Classification Search
CPC ...... G01N 37/00; G01N 1/4077; G01N 33/00; B01L 3/50857; B01L 3/502761; G02B 21/34
(Continued)

(56) References Cited

U.S. PATENT DOCUMENTS

| 2005/0052509 A1* | 3/2005 | Gilligan | ............ B01L 3/50273 |
|---|---|---|---|
| | | | 347/85 |
| 2005/0066812 A1* | 3/2005 | Vesper | ............... B01D 19/0031 |
| | | | 95/46 |

(Continued)

FOREIGN PATENT DOCUMENTS

| JP | 2008-000079 A | 1/2008 |
|---|---|---|
| JP | 2011-163830 A | 8/2011 |

(Continued)

OTHER PUBLICATIONS

International Search Report and Written Opinion of PCT Application No. PCT/JP2019/047523, issued on Mar. 3, 2020, 09 pages of ISRWO.

*Primary Examiner* — Arlen Soderquist
(74) *Attorney, Agent, or Firm* — CHIP LAW GROUP

(57) ABSTRACT

A technology for efficiently discharging a bubble present in a fluid in a chamber is provided. There is provided a bubble discharging method carried out in a chamber including a microchip that includes at least one well or through hole to divide a space into a first space and a second space, the bubble discharging method including a pressurizing step of applying a positive pressure to a fluid in the chamber, and a valve opening/closing step of operating a valve for opening/closing a first flow path connected to the first space and/or a second flow path connected to the second space.

14 Claims, 6 Drawing Sheets

(52) U.S. Cl.
CPC ............... *B01L 2300/0819* (2013.01); *B01L 2400/0487* (2013.01)

(58) Field of Classification Search
USPC .......................................... 422/502; 436/165
See application file for complete search history.

(56) References Cited

U.S. PATENT DOCUMENTS

| | | | | |
|---|---|---|---|---|
| 2006/0227512 | A1* | 10/2006 | Dishongh | F28F 27/02 257/E23.098 |
| 2007/0163663 | A1* | 7/2007 | Strand | F16K 99/0042 137/806 |
| 2007/0264705 | A1* | 11/2007 | Dodgson | B01L 3/502761 435/283.1 |
| 2008/0038713 | A1* | 2/2008 | Gao | G01N 33/6845 435/287.1 |
| 2009/0233351 | A1* | 9/2009 | Akechi | B01D 19/0031 324/693 |
| 2013/0130262 | A1* | 5/2013 | Battrell | B01L 3/50273 435/6.12 |
| 2020/0330989 | A1* | 10/2020 | Masuhara | G01N 15/1404 |
| 2021/0364410 | A1* | 11/2021 | Hosokawa | G01N 15/1429 |

FOREIGN PATENT DOCUMENTS

| | | | | |
|---|---|---|---|---|
| JP | 2014-226623 A | | 12/2014 | |
| WO | 2008/096563 A1 | | 8/2008 | |
| WO | WO-2014081840 A1 | * | 5/2014 | ........ B01L 3/502715 |
| WO | WO-2019049944 A1 | * | 3/2019 | ........ B01L 3/50273 |

* cited by examiner

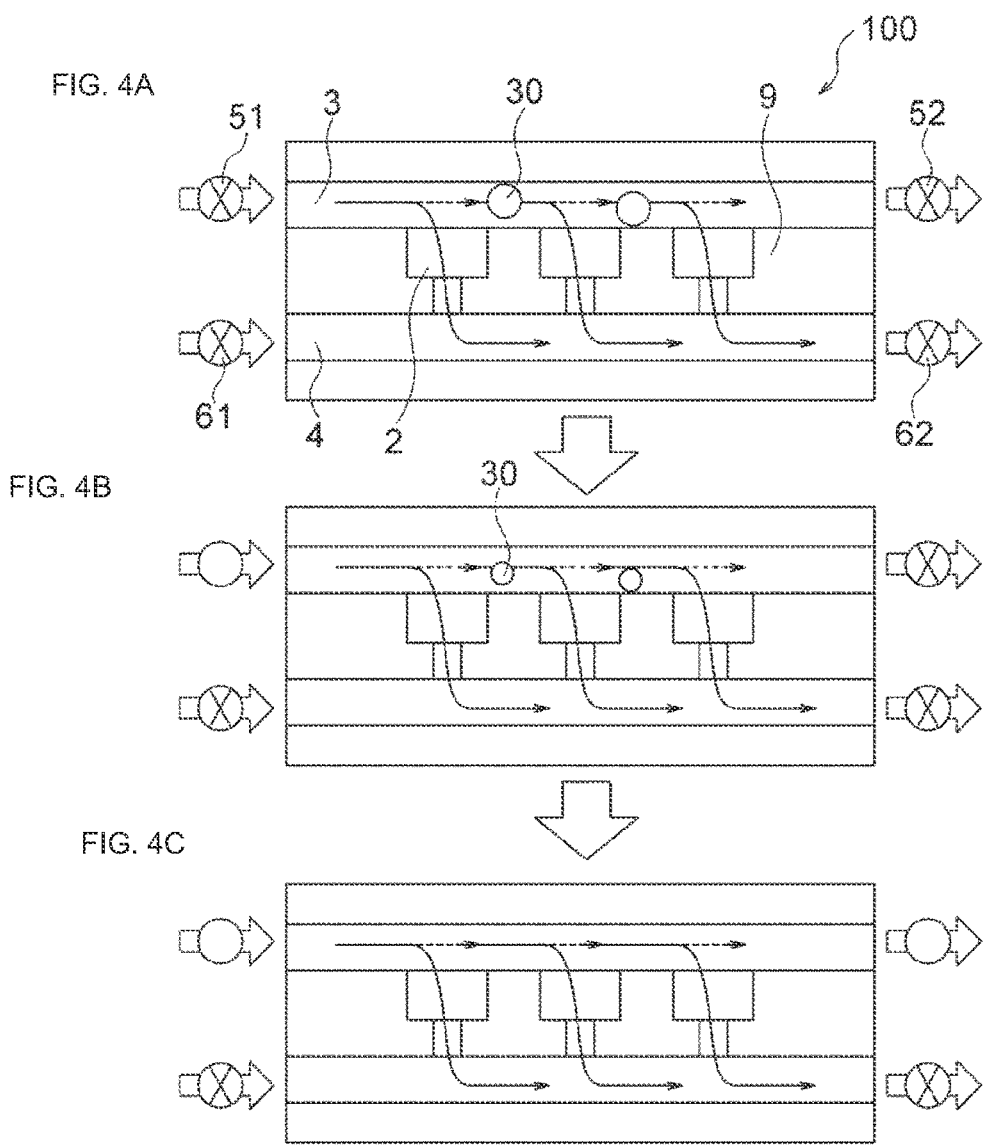

BUBBLE DISCHARGING METHOD, PARTICLE TRAPPING APPARATUS, AND PARTICLE ANALYZING APPARATUS

CROSS REFERENCE TO RELATED APPLICATIONS

This application is a U.S. National Phase of International Patent Application No. PCT/JP2019/047523 filed on Dec. 4, 2019, which claims priority benefit of Japanese Patent Application No. JP 2019-011785 filed in the Japan Patent Office on Jan. 28, 2019. Each of the above-referenced applications is hereby incorporated herein by reference in its entirety.

TECHNICAL FIELD

The present technology relates to a bubble discharging method, a particle trapping apparatus, and a particle analyzing apparatus.

Attention has been drawn to technologies for analyzing particles such as single cells. Technologies for analyzing particles such as single cells may include trapping a single cell into each of a large number of microwells arranged on a plane, and individually observing the morphology of each cell to analyze characteristics of each cell, and/or analyzing the reaction of each cell with a reagent using, for example, fluorescence or the like as an indicator.

Examples of a commercially available apparatus used in a technology for analyzing particles such as single cells may include AS ONE Cell Picking System (AS ONE Corporation). In an analysis technology employing the apparatus, a cell suspension is applied to a microchamber having a large number of wells each having a size for containing a single cell, and each cell is settled in each of the wells. Then, a cell in each well is collected and/or analyzed individually. The well is disposed on a chip in the microchamber. As the chip, multiple types of chips corresponding to cell sizes are made available. For example, a chip (about 80,000 wells) in which φ30 μm wells are arranged at a pitch of 80 μm in the X and Y directions and a chip (about 300,000 wells) in which φ10 μm wells are arranged at a pitch of 30 μm in the X and Y directions are available. Characteristics of each individual cell isolated in each well by the apparatus are observed by means such as fluorescence detection. Then, a cell of interest may be extracted from the well by a micromanipulator, transferred to a 96-well/384-well plate, and subjected to a more detailed analysis such as sequencing, for example.

Furthermore, for example, the technology described in Patent Document 1 below may be cited as a technology for trapping a cell in a well. Patent Document 1 listed below describes "a micro fluid device capable of trapping circulating tumor cells (CTC) included in a blood sample by using a size-selective micro cavity array, the micro fluid device including: an upper member in which a sample inlet, a sample outlet, and a micro flow path communicating the sample inlet with the sample outlet are formed and an open window for the size-selective micro cavity array is disposed at a position corresponding to a part of the micro flow path; a micro cavity array holding unit including the size-selective micro cavity array having a fine CTC-trapping through hole of which hole diameter, hole number, and placement are controlled, and a tight seal holding the size-selective micro cavity array at a position corresponding to a lower side of the open window of the upper member; and a lower member in which a suction open window disposed at a position corresponding to a lower side of the size-selective micro cavity array and a suction flow path communicating the suction open window with a suction opening are formed."

In addition, Patent Document 2 states that an object is providing a microchip inspection system capable of removing a bubble that may be occasionally formed within a liquid in a detection unit by, for example, heating the detection unit, thereby achieving highly accurate detection. In addition, Patent Document 2 states that "the object is achieved by a microchip inspection system including: a microchip which contains at least a target substance and a reagent that binds specifically to the target substance, in which the target substance reacts with the reagent and the reaction is detected by a detection unit; a microchip containing unit capable of containing the microchip; a photo detection unit which is provided corresponding to the detection unit in the microchip contained in the microchip containing unit and which detects the reaction; debubbling means that removes bubbles in the detection unit in the microchip contained in the microchip containing unit; and a control unit that controls the photo detection unit so that the reaction is detected after the debubbling means is activated."

CITATION LIST

Patent Document

Patent Document 1: Japanese Patent Application Laid-Open No. 2011-163830
Patent Document 2: WO 2008/096563 A

SUMMARY OF THE INVENTION

Problems to be Solved by the Invention

With the recent increase in interest in the life science field, fluid samples for flow cytometry, for example, are more often used. However, handling a fluid inevitably involves bubbles entrained into a flow path, and it is difficult to discharge the bubbles from the flow path. The inventor of the present disclosure noticed the fact that such entrained bubbles affect the original purpose, which is measurement or the like, and in worst cases, the measurement may provide a false negative or false positive result to adversely affect a diagnosis or decision.

However, as far as the inventor of the present disclosure knows, as of the present time, a countermeasure against entrained bubbles is merely urging the entrained bubbles to be dissolved into a liquid by pressurization to increase the concentration of a saturated gas as described in Patent Document 2 above (for example, paragraphs [0089], [0095], and the like).

Since the concept shown in Patent Document 2 is that a liquid containing a bubble dissolved in the liquid by pressurization is discharged as a whole, the inventor of the present disclosure considers that it is difficult to dissolve a bubble that has become extremely large into the liquid. If a bubble that has become extremely large is to be dissolved, a much higher pressure is needed. The inventor of the present disclosure believes that, in this case, such pressurization is more likely to cause troubles such as damage to the apparatus (for example, damage or the like to a flow path in the microchip, a chamber including the microchip, or the like).

Thus, the inventor of the present disclosure believes that a new attempt to discharge bubbles entrained in a fluid is needed and that a technology for discharging such entrained bubbles will be in increasing demand in the future.

Therefore, a main object of the present technology is to provide a technology for efficiently discharging bubbles present in a fluid in a chamber.

Solutions to Problems

According to the present technology, there can be provided a bubble discharging method carried out in a chamber including a microchip that includes at least one well or through hole to divide a space into a first space and a second space, the bubble discharging method including:
a pressurizing step of applying a positive pressure to a fluid in the chamber; and
a valve opening/closing step of operating a valve for opening/closing a first flow path connected to the first space and/or a second flow path connected to the second space.

Furthermore, according to the present technology, the microchip may include a particle trapping chip that includes a particle trapping region including at least one well or through hole.

Furthermore, in a configuration according to the present technology, the first flow path may include a flow path that is connected to a first supply valve from which a fluid is supplied and to a first discharge valve from which the fluid is discharged, and/or
the second flow path may include a flow path that is connected to a second supply valve from which the fluid is supplied and to a second discharge valve from which the fluid is discharged.

According to the present technology, the valve opening/closing step may include a step of opening/closing the supply valve and/or the discharge valve after a positive pressure is applied to the fluid in the chamber and discharging a bubble from the chamber.

According to the present technology, the pressurizing step and the valve opening/closing step may be repeatedly performed.

Moreover, according to the present technology, a bubble analyzing step of analyzing a bubble in the chamber on the basis of information acquired by imaging the bubble in the chamber may be included.

According to the present technology, in the bubble analyzing step, it may be determined whether or not a bubble in the chamber meets a predetermined condition, and, if it is determined that the bubble meets the predetermined condition, the pressurizing step and the valve opening/closing step may be performed.

In a configuration according to the present technology, in the pressurizing step, the fluid in the chamber may be pressurized in the state where the supply valve is opened and valves other than the supply valve are closed, and
in the valve opening/closing step, after the supply valve is closed, at least any one of the closed valves may be intermittently opened.

In a configuration according to the present technology, in the pressurizing step, the fluid in the chamber may be pressurized in the state where the supply valve is opened and valves other than the supply valve are closed, and
in the valve opening/closing step, at least any one of the closed valves may be opened.

According to the present technology, the particle may be a single cell.

Furthermore, according to another aspect of the present technology, there may be provided a particle trapping apparatus including:
a pressure control unit that performs control, in a chamber including a microchip that includes at least one well or through hole to divide a space into a first space and a second space,
so as to perform a pressurizing step of applying a positive pressure to a fluid in the chamber and
a valve opening/closing step of operating a valve for opening/closing a first flow path connected to the first space and/or a second flow path connected to the second space, and to discharge a bubble in the chamber,
in which
the particle trapping apparatus traps a particle into the well or the through hole.

According to the present technology, the microchip may be disposed in such a way that an upper side of the first space is gradually higher in a discharge direction.

According to the present technology, the microchip may be disposed in such a way that a cross-sectional area of the microchip across the width direction is gradually larger in the discharge direction.

According to another aspect of the present technology, there may be provided a particle analyzing apparatus including:
a pressure control unit that performs control, in a chamber including a microchip that includes at least one well or through hole to divide a space into a first space and a second space,
so as to perform a pressurizing step of applying a positive pressure to a fluid in the chamber and
a valve opening/closing step of operating a valve for opening/closing a first flow path connected to the first space and/or a second flow path connected to the second space, and to discharge a bubble in the chamber;
an observation unit that images, with a microscope, a bubble in the chamber and/or a particle trapped in the well or the through hole; and
an analysis unit that conducts an analysis relating to the bubble and/or the particle trapped on the basis of information acquired from the observation unit.

BRIEF DESCRIPTION OF DRAWINGS

FIGS. 4A, 4B, and 4C are schematic diagrams illustrating an example of the bubble discharging method according to the present technology.

MODE FOR CARRYING OUT THE INVENTION

Figure 1:
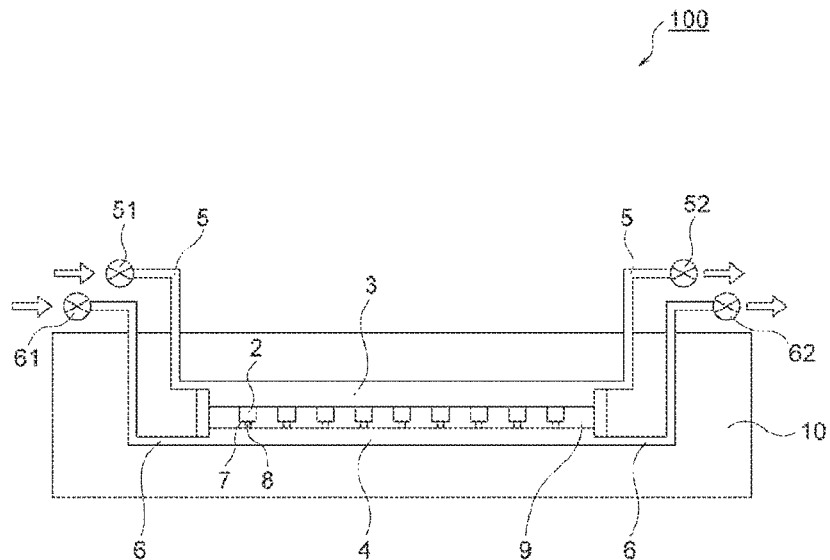
FIG. 1 is a diagram illustrating an example of a chamber used for a bubble discharging method according to the present technology.

A preferred mode for carrying out the present technology will now be described with reference to the drawings.

The embodiments described below show an example of representative embodiments of the present technology, and the scope of the present technology is not construed as being limited by the embodiments. Note that descriptions will be provided in the order mentioned below. Note that identical reference symbols are given to identical or similar elements or members in the drawings and duplicate descriptions are omitted as appropriate. Furthermore, effects provided by the present technology are not necessarily limited to the effects described in the individual items, but may be any of the effects described herein.

1. Bubble discharging method according to the present technology
   <1-1. Bubble discharging method of first embodiment of the present technology>
   <1-2. Bubble discharging method of second embodiment of the present technology>
   <1-3. Bubble discharging method of third embodiment of the present technology>
   <1-4. Other embodiments employing bubble discharging method of the present technology>
   <1-4 (A) Example 1 of particle trapping method and particle analyzing method of the present technology>
   <1-4 (B) Example 2 of particle trapping method and particle analyzing method of the present technology>
   <1-5. Examples 1 to 3 of bubble discharging method of the present technology>
2. Apparatus according to the present technology
   <2-1. Apparatus including chamber and pressure control unit according to the present technology>
   <2-2. Chamber and microchip according to the present technology>
   <2-3. Particle trapping apparatus according to the present technology>
   <2-4. Particle analyzing apparatus according to the present technology>
   <2-5. Example 1 of apparatus according to the present technology>
   <2-6. Example 2 of apparatus according to the present technology>

1. Bubble Discharging Method According to the Present Technology

The present technology provides a bubble discharging method carried out in a chamber including a microchip that includes at least one well or through hole to divide a space into a first space and a second space (see FIGS. 1, 2, 3A, 3B, 3C, 4A, 4B, 4C, and 5, for example). The bubble discharging method includes a pressurizing step of applying a positive pressure to a fluid in the chamber, and a valve opening/closing step of operating a valve for opening/closing a first flow path connected to the first space and/or a second flow path connected to the second space. As a result, bubbles present in the fluid in the chamber can be efficiently discharged.

In the present technology, a chamber refers to a structure provided with a space for a fluid to move. The fluid is not particularly limited, and the fluid may be either a liquid or a gas. Furthermore, the fluid may contain particles, and details of the particles are described later. The microchip may be a microchip for trapping particles, and the microchip preferably has a particle trapping region that includes at least one well or through hole.

In addition, spaces for the well, through hole, first space, second space, first flow path, second flow path, and the like that may be included in the chamber of the present technology may employ configurations that allow a fluid to move appropriately, and these configurations are not particularly limited.

The chamber of the present technology preferably has a configuration in which the chamber includes at least one well or through hole to divide a space into the first space and the second space. In the present technology, the first space may be a flow path along which a fluid can appropriately move or a portion including the flow path. Furthermore, in the present technology, the second space may be a flow path along which a fluid can appropriately move or a portion including the flow path.

It is preferable that the chamber of the present technology has a region that at least includes one well or one through hole (hereinafter also referred to as a "well/through hole region"). The well or the through hole may communicate with the first space and/or the second space. A hole may be disposed in the well or through hole to communicate with the first space and/or the second space, and the well or through hole may communicate with the first space and/or the second space via the hole. Although details of the shape and the like of the well or the through hole are described later, the well or the through hole includes an opening into which particles will flow, and the opening is preferably open upward from the viewpoint of trapping particles, which flow in the settling direction by their own weight and the like. However, the opening may open upward or downward. The well/through hole region can also function as a particle trapping region that includes at least one well or through hole.

In addition, the chamber of the present technology may employ a configuration that includes a microchip having at least one well or through hole. Furthermore, the present technology may employ a configuration in which the microchip has at least one well or through hole to divide a space into the first space and the second space, or may employ a configuration in which the chamber includes such microchip.

The bubble discharging method of the present technology at least includes performing the pressurizing step and the valve opening/closing step in the chamber. More preferably, the present technology further includes performing a bubble analyzing step of analyzing bubbles in the chamber. From the viewpoint of efficiently discharging bubbles, it is preferable to perform the bubble analyzing step in the bubble discharging method to understand the state of bubbles in the chamber and handle the bubbles appropriately.

The bubble discharging method of the present technology is preferably carried out with an apparatus that has a configuration in which the first flow path and the second flow path in the chamber include a first valve and a second valve, respectively, and has a configuration in which a pressure control unit controlling the pressure in the chamber is included. The number of valves of each of the first valve and the second valve may be one or more. From the viewpoint of fulfilling supply and discharge, the number of valves of each of the first valve and the second valve is preferably at least two or more, respectively.

The first flow path of the present technology is preferably a flow path connected to a first supply valve from which a fluid is supplied and to a first discharge valve from which the fluid is discharged. In addition, in a preferred configuration, the first flow path of the present technology is connected to the first space and is connected to the first supply valve from which a fluid is supplied and to the first discharge valve from which the fluid is discharged. Preferably, a plurality of first flow paths is disposed, and more preferably, one first flow path is disposed on the first supply valve side and one first flow path is disposed on the first discharge valve side. In a preferred configuration, there is a first space between the first flow path on the first supply valve side and the first flow path on the first discharge valve side, and the first space is connected to both of the first flow paths. By opening/closing the first supply valve and the first discharge valve, fluid control such as control of the flow velocity and fluid pressure in the chamber (mainly in the first space) can also be easily performed.

The second flow path of the present technology is preferably a flow path connected to a second supply valve from which a fluid is supplied and to a second discharge valve from which the fluid is discharged. In addition, in a preferred configuration, the second flow path of the present technology is connected to the second space and is connected to the second supply valve from which a fluid is supplied and to the second discharge valve from which the fluid is discharged. Preferably, a plurality of second flow paths is disposed, and more preferably, one second flow path is disposed on the second supply valve side and one second flow path is disposed on the second discharge valve side. In a preferred configuration, there is a second space between the second flow path on the second supply valve side and the second flow path on the second discharge valve side, and the second space is connected to both of the second flow paths. By opening/closing the second supply valve and the second discharge valve, fluid control such as control of the flow velocity and fluid pressure in the chamber (mainly in the second space) can also be easily performed.

Furthermore, it is preferable to employ a configuration in which the chamber used for the bubble discharging method of the present technology includes a region containing a well or through hole between the first space connected to the first flow path and the second space connected to the second flow path. It is preferable that the first space and the second space are disposed so as to sandwich the well/through hole region like a sandwich structure, and a fluid in one of the first space and the second space is allowed to move to the other one of the first space and the second space via the well/through hole region.

The bubble discharging method of the present technology makes it possible to more efficiently remove entrained bubbles in the chamber configured as above by controlling the pressure in the chamber.

Note that a fluid such as a buffer solution is flowed into the chamber prior to the pressurizing step and the valve opening/closing step according to the present technology. Although entrained bubbles may be discharged to some extent by flowing such fluid into the chamber, in practice, bubbles often remain in the chamber, and it is difficult to completely discharge the bubbles. Carrying out the bubble discharging method of the present technology can efficiently discharge such bubbles entrained into the chamber. In addition, carrying out the bubble discharging method of the present technology discharges bubbles from the chamber, with the result that the inside of the chamber including the well/through hole region, the first space, and the second space is filled with a fluid containing a much reduced number of bubbles. According to the present technology, particle trapping, particle analysis, and the like can be conducted with the fluid containing a much smaller number of bubbles, thereby improving the accuracy thereof.

In the present technology, the first space and the second space are disposed in the chamber, and there may be a bubble entrained in the first space or the second space.

In a case where a bubble is present in the first space in the chamber, it is preferable to use the first valve to discharge the bubble. More specifically, from the viewpoint of efficiency, it is more preferable to use the first supply valve and the first discharge valve to discharge the bubble present in the first space in the chamber.

In addition, in a case where a bubble is present in the second space in the chamber, it is preferable to use the second valve to discharge the bubble. More specifically, from the viewpoint of efficiency, it is more preferable to use the second supply valve and the second discharge valve to discharge the bubble present in the second space in the chamber.

Note that, in the present technology, the first space may be disposed on the upper side so that the first space and the second space serve as an upper flow path and a lower flow path, respectively, or conversely, the second space may be disposed on the upper side so that the first space and the second space serve as a lower flow path and an upper flow path, respectively.

The following describes Examples 1 to 3 of a basic step including the pressurizing step and the valve opening/closing step in the present technology (see FIGS. 3A, 3B, 3C, 4A, 4B, 4C, and 5, for example); however, the present technology is not limited thereto. In addition, in the present technology, the supply side refers to the side on which a fluid is supplied, and more specifically, the valve supply side. In addition, in the present technology, the discharge side refers to the side on which a fluid is discharged, and more specifically, the valve discharge side.

Example 1 of the basic step (see FIGS. 3A, 3B, and 3C, for example): With all the valves at inlets and outlets (on the supply side and discharge side) closed, open one of the valves. Apply a positive pressure to the fluid from the opened valve to contract a bubble in the chamber, and then close the valve. Then, open one discharge valve. The bubble is caused to expand, moves by a certain distance, and stops. Then, open a discharge valve intermittently to cause the bubble to expand and contract repeatedly. Through the expansion and contraction, the bubble moves by a certain distance and stops repeatedly. Through the repetition, the bubble is caused to move to an outlet on the discharge side. For example, in a more specific example, when the discharge valve is opened, a contracted bubble is expanded and moves to the discharge side by a certain distance and stops; when the discharge valve is closed, the expanded bubble is contracted while stopping; and when the discharge valve is opened again, the bubble is expanded and moves to the discharge side and stops again. It is preferable that the supply valve and the discharge valve used here are connected to the same space via a flow path or the like. In this way, it is preferable to perform the pressurizing step of applying a positive pressure and the valve opening/closing step of opening/closing a valve intermittently, and more preferably, the pressurizing step and the valve opening/closing step are repeated. As a result, bubbles can be discharged from the chamber.

Example 2 of the basic step (see FIGS. 4A, 4B, and 4C for example): Close all the valves at inlets and outlets (on the supply side and discharge side), and then open one of the valves. Apply a positive pressure to the fluid from the opened valve to contract a bubble and, without closing the valve, open one discharge valve while the bubble is kept contracted so that the bubble is discharged from an outlet on the discharge side with momentum. It is preferable that the supply valve and the discharge valve used here are connected to the same space via a flow path or the like. In this way, it is preferable to perform the pressurizing step of applying a positive pressure and the valve opening/closing step of opening a valve under pressurized condition. As a result, bubbles can be discharged from the chamber.

Example 3 of the basic step (see FIG. 5, for example): Bubbles can be guided to the outlet in a configuration in which the height of the upper flow path gradually increases toward the outlet of the first discharge valve. To take advantage of characteristics of bubbles, that is, the tendency to move in a direction opposite to the direction of their own weight, the upper flow path is sloped such that the height gradually increases toward the outlet. The upper flow path refers to either the first space or the second space that is located on the upper side. By utilizing the structural characteristics, bubbles can be discharged from the chamber.

In the present technology, an appropriate combination of Examples 1 to 3 of the basic step, such as a combination of Examples 1 and 2 of the basic step, is employed to make it possible to discharge bubbles out of the chamber with a high probability.

The following describes the bubble discharging method of the present technology in more detail.

The pressurizing step of the present technology includes applying a positive pressure to a fluid in the chamber.

Applying a positive pressure to the fluid in the chamber may cause a bubble in the fluid in the chamber to contract or dissolve in the fluid. For example, the bubble contracted by the pressurizing step is less likely to come into contact with the inner wall surface or the like when moving through the fluid, and thus can more easily move with a flow in the fluid. Furthermore, for example, the bubble being in contact with and adhering to the inner wall surface is contracted by the pressurizing step, and the contracted bubble comes off the inner wall surface or has a smaller contact surface on the inner wall surface, and thus the contracted bubble can more easily move with a flow of the fluid.

In a case where a positive pressure is applied in the pressurizing step, the positive pressure may be applied from either of the fluid supplying side and the fluid discharging side, without specific limitation. More preferably, in a case where a positive pressure is applied, it is preferable to apply the pressure from the fluid supply side (more specifically, the valve supply side) partly because a bubble is allowed to move to the fluid discharging side (more specifically, the valve discharge side) when a positive pressure is applied.

The means for applying a positive pressure is not particularly limited, and examples thereof include an apparatus (for example, a pump or the like) capable of adjusting the flow rate or fluid pressure of a fluid. The means for applying a positive pressure may be disposed separately from the valve opening/closing means, or may be disposed such that a pump, a valve, and the like are used in a shared manner with the valve opening/closing means.

Furthermore, it is preferable that the pressurization of a fluid or the like performed by the means for applying a positive pressure can be controlled by the pressure control unit. Furthermore, a flow path for applying a positive pressure may be additionally provided in the chamber separately from the first flow path and the second flow path and connected to the first space or the second space. Alternatively, the first flow path or the second flow path may be used as the flow path for applying a positive pressure, whereby the configuration inside the chamber can be simplified.

The valve opening/closing step of the present technology preferably includes operating the valve for opening/closing the first flow path connected to the first space and/or operating the valve for opening/closing the second flow path connected to the second space. Opening a valve after the pressurizing step causes a bubble in the chamber to move toward the side on which the valve is opened. It is preferable that a valve on the fluid discharging side (for example, the valve discharge side) is opened, and thus a bubble is allowed to move toward the fluid discharging side when the valve is opened. In addition, it is preferable to open a discharge valve connected to the upper space (specifically, the first space or the second space) because bubbles float in a fluid. Discharge of bubbles may be facilitated by suction provided by suction means such as a pump connected to a valve on the fluid discharging side.

Moreover, with respect to the opened valve, by closing the valve and then intermittently opening and closing the valve repeatedly, a bubble is caused to expand and contract and thus allowed to move toward the discharge side. During the repetition of intermittent opening and closing of the valve, the above-described pressurizing step may be performed again to pressurize the inside of the chamber (in particular, the first space and/or the second section). It is preferable to perform the pressurization because a bubble can move by a longer distance, thereby efficiently discharging the bubble.

It is preferable that opening and closing of a valve (for example, an opening/closing valve, a flow rate regulating valve, a fluid pressure regulating valve, or the like or a combination of two or more thereof or the like) in the chamber can be controlled by the pressure control unit. As a result, valves for opening and closing the first flow path and/or the second flow path in the chamber can be operated. The fluid that is moving in the first space and the second space connected to the first flow path and the second flow path, respectively, can be controlled (for example, the flow rate and fluid pressure can be controlled) by such opening and closing, whereby bubbles in the chamber can be more efficiently discharged.

In the valve opening/closing step in the present technology, it is preferable to open/close the supply valve and/or the discharge valve as appropriate after a positive pressure is applied to a fluid in the chamber. As a result, a bubble in the chamber is caused to expand and contract and thus allowed to move, thereby efficiently discharging the bubble.

Moreover, it is preferable to repeatedly perform the pressurizing step and the valve opening/closing step of the present technology. The pressurizing step allows a bubble in the chamber to contract or dissolve in the fluid, and the subsequent valve opening/closing step allows a bubble present in the chamber to move toward the discharge side. Moreover, repetition of the pressurizing step and the valve opening/closing step sums up the moving distance/turn of a bubble, thereby efficiently moving a bubble toward the discharge side. It is preferable to continue the repetition until a bubble in the chamber is discharged. To determine the extent of the repetition, it is desirable that a particle analyzing step is performed in parallel and an observation unit observes the state of a bubble moving in the chamber.

Repetition of the pressurizing step and the valve opening/closing step allows for control of the fluid (the flow velocity and fluid pressure, for example) in the chamber, and as a result of the control, a bubble in the chamber can be efficiently discharged.

In the present technology, it is preferable to further perform the bubble analyzing step in addition to the pressurizing step and the valve opening/closing step. By the bubble analyzing step, bubbles in the chamber can be more satisfactorily and more efficiently discharged. In the bubble discharging method of the present technology, the ordinal and arrangement of the bubble analyzing step are not particularly limited, and the bubble analyzing step may be performed at the same time as, or at a different time from, the time when the pressurizing step or the valve opening/closing step is performed. It is preferable that the bubble analyzing step is performed in parallel with the pressurizing step and the valve opening/closing step because it is easier to track the state of bubbles and to determine in which state the pressurizing step and the valve opening/closing step are to be performed.

In the bubble analyzing step of the present technology, a bubble in the chamber is analyzed on the basis of the information acquired by imaging the bubble in the chamber. Determination related to the analysis of a bubble in the chamber may be made on the basis of the acquired information regarding imaging provided by the observation unit or the analysis unit. If a bubble is found to be present in the chamber in the bubble analyzing step on the basis of an analysis result, it is preferable to instruct the pressure control unit or the like to perform the pressurizing step and the valve opening/closing step as appropriate until no bubble is present in the chamber. Additionally, performing the bubble analyzing step ensures that bubbles present in a fluid in the chamber are discharged more reliably and more efficiently, thereby improving the accuracy of particle trapping, particle analysis, and the like.

Furthermore, in the bubble analyzing step of the present technology, it is preferable to determine whether or not a bubble in the chamber meets a predetermined condition. If it is determined that the bubble meets a predetermined condition in the bubble analyzing step, it is preferable to give an instruction that the pressurizing step and the valve opening/closing step should be performed. The unit that makes the determination is not particularly limited, and the determination may be made by the analysis unit, the pressure control unit, the observation unit, or the central control unit that presides these units. Furthermore, in a case where predetermined conditions are to be stored, the storing unit is not particularly limited. The predetermined conditions may be stored not only in any of these units mentioned above but also in an external or internal storage unit. As a result, bubbles in the chamber can be efficiently discharged under such control.

The predetermined conditions may be set as appropriate, or the conditions may be set or re-set by accumulating bubble information and the like in an artificial intelligent (AI) system.

In the present technology, the size or the number of bubbles, on the basis of which it is determined that a bubble is present in the chamber, are not particularly limited, and thus any size or number may be set as appropriate. The size of a bubble, on the basis of which it is determined that a bubble is present in the chamber, can be set as appropriate in advance in individual units such as the storage unit and the analysis unit.

The number of bubbles to be used for making the above-mentioned determination is not particularly limited; however, from the viewpoint of efficiency, it is preferable that the state of bubbles such as the number and locations of bubbles is output to the pressure control unit if one or more bubbles that are not dissolved in the fluid preferably when being pressurized are present in the chamber.

The bubble size to be used for making the above-mentioned determination is not particularly limited; however, it is preferable to carry out the present technology when the size of a bubble before a positive pressure is applied is preferably φ50 μm or larger, and more preferably φ20 μm or larger. In a case where a bubble in the chamber is not larger than a certain size, it is preferable, from the viewpoint of efficiency, to discharge the bubble by applying a positive pressure to the fluid in the chamber so that the bubble is dissolved in the fluid.

In addition, in a case where it is determined that a bubble after a positive pressure is applied is larger than a certain size, it is preferable, from the viewpoint of efficiency, to output an instruction to the pressure control unit to employ a step of discharging the bubble at a time (for example, the second embodiment). It is preferable to perform the step of discharging a bubble at a time when the size of the bubble to which a positive pressure has been applied is preferably φ200 μm or larger, and more preferably φ500 μm or larger.

In addition, examples of the means for imaging a bubble in the chamber include, without particular limitation, a microscope, an imaging apparatus, and the like as described later. The means for imaging a bubble in the chamber may be the observation unit capable of analyzing particles, or may be configured to cooperate with the analysis unit that analyzes particles and bubbles, or imaging may be controlled by the observation unit or the analysis unit.

As the means for analyzing a bubble, it is preferable to employ a component such as the analysis unit or the observation unit as described later, and the information acquired by imaging a bubble in the chamber may be analyzed.

It is preferable that the means for analyzing a bubble according to the present technology is configured to acquire bubble analysis information from another unit to analyze the state of a bubble in the chamber and to make comparative review of methods for efficiently discharging a bubble in the chamber.

In the bubble analyzing step of the present technology, an instruction to set and apply bubble discharge conditions may be given. As the bubble discharge conditions set out in this step, selecting any of the individual procedures and steps for discharging bubbles in the present technology (for example, the first to third embodiments or the like) and selecting a valve to be used or the like may be set as appropriate in addition to those conditions described above; however, the present technology is not limited thereto.

For example, in a case where it is determined in a bubble analysis that a bubble is equal to or less than a predetermined condition, there may be given an instruction that the pressure control unit or the like should select and carry out the bubble discharging method of the first embodiment. In addition, there may be given an instruction that the pressure control unit or the like should select and carry out repeatedly the bubble discharging method of the first embodiment until the conditions for determining in the bubble analysis that there is no bubble are satisfied.

Furthermore, in a case where it is determined in a bubble analysis that a larger number of bubbles than a predetermined number are present, there may be given an instruction that the pressure control unit or the like should select and carry out the bubble discharging method of the second embodiment. After that, in a case where it is determined in the bubble analyzing step that the bubbles are equal to or less than a predetermined condition, there may be given an instruction that the pressure control unit or the like should switch to the bubble discharging method of the first embodiment.

Note that the bubble discharging method of the present technology can be stored in the form of a program in a hardware resource provided with a control unit including a CPU and the like for various devices, a storage medium (a USB memory, HDD, CD, network server, or the like), and others, and the bubble discharging method can be implemented by the control unit. Furthermore, the present technology can be in the form of a program for causing a computer to function as the bubble discharging method of the present technology.

According to the present technology, bubbles present in a fluid in the chamber can be efficiently discharged. As a result, the accuracy, the efficiency, and the like of particle analysis, particle trapping, and the like can be improved in an apparatus or system that employs a flow path system for assaying, trapping, analyzing, and the like of particles. For example, while conventional technologies do not make it possible to fractionate and trap particles such as cells with regard to a region where a bubble is entrained, the present technology makes it possible to discharge entrained bubbles, thereby increasing the number of particles such as cells that can be fractionated and trapped. For example, while an image analysis such as imaging that involves counting particles such as cells on the basis of the particle shape may produce a false positive result if a bubble equal to particles such as cells in size is entrained, the present technology can reduce, prevent, or avoid producing such result because of the capability to discharge entrained bubbles. For example, in a case where particles such as cells are trapped and an image is obtained by imaging the particles such as cells that have been trapped, as compared with the case where bubbles are entrained, the present technology provides a better contrast because of the capability to discharge entrained bubbles.

Note that effects provided by the present technology are not necessarily limited to the effects described above, but may be any of the effects described herein.

1-1. Bubble Discharging Method of First Embodiment of the Present Technology The following describes a bubble discharging method according to a first embodiment of the present technology (see FIGS. 2, 3A, 3B, and 3C, for example).

No specific limitation is imposed on the start of the bubble discharging method of the present technology as long as a fluid is present in the chamber. For example, the bubble discharging of the present technology is started when any of valves 51, 52, 61, and 62 is opened to cause a fluid to flow into the chamber or in the state where a fluid is already flowed into the chamber. The bubble discharging method of the present technology is desirably carried out at least once even in a case where no bubble is recognized to be present in the chamber. As a result, a bubble that may have been missed by observation can be discharged, thereby improving the accuracy of particle trapping and particle analysis to be conducted later.

Figure 3A:
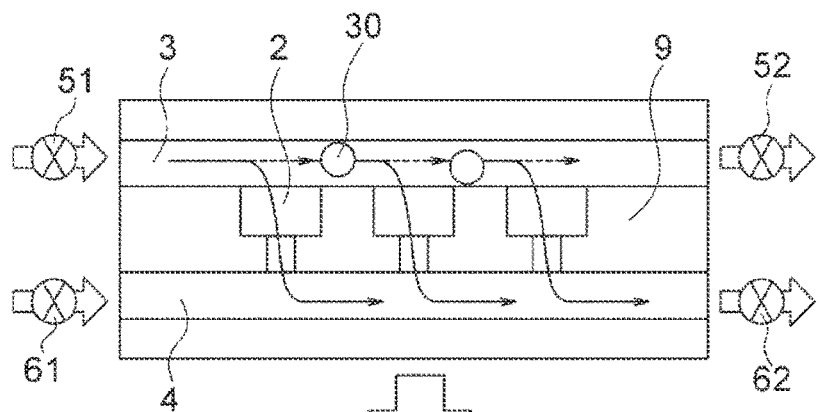
FIGS. 3A, 3B, and 3C are schematic diagrams illustrating an example of the bubble discharging method according to the present technology.

In the first embodiment of the present technology, it is preferable to close all the valves 51, 52, 61, and 62 in the presence of a fluid in the chamber (see FIG. 3A, for example). Then, a supply valve is opened for the purpose of applying a positive pressure, and in the state where the valves other than this supply valve are closed, a positive pressure is applied to the fluid in the chamber (see FIG. 3B: pressurizing step). Applying a positive pressure causes a bubble 30 in the chamber to contract into a smaller bubble or to dissolve in the fluid.

Note that a supply valve connected to the space where the bubble 30 is present is preferably used for applying a positive pressure. For example, in a case where a bubble is present in a first space 3, the first supply valve 51 is preferably used, and in a case where a bubble is present in a second space 4, the second supply valve 61 is preferably used. In addition, in a case where the first space 3 is located on the upper side, the first supply valve 51 is preferably used because bubbles tend to float.

Furthermore, in the valve opening/closing step, the above-mentioned supply valve is closed, and all the valves 51, 52, 61, and 62 are closed. At least any one of the closed valves is then opened (see FIG. 3C, for example). When a valve is opened, an entrained bubble moves toward the opened valve while expanding.

Here, it is preferable to open a discharge valve connected to the space (the first space or the second space) connected to the supply valve that has been used for applying a positive pressure. For example, the first discharge valve 52 is preferably opened in the case of the first supply valve 51, and the second discharge valve 62 is preferably opened in the case of the second supply valve 61. When a discharge valve is opened, the entrained bubble further moves toward the discharge side.

Through opening/closing of discharge valve, a bubble entrained in the chamber expands when the discharge valve is opened, and contracts and simultaneously moves toward the discharge valve when the discharge valve is closed. Regarding the movement of a bubble in this step, the bubble moves when expanding and stops when contracting.

Furthermore, a discharge valve is preferably opened and closed intermittently. The intermittent opening/closing allows the bubble to move toward the discharge valve while moving and stopping repeatedly by expanding and contracting. The intermittent opening/closing may be done by using the same discharge valve (for example, the first discharge valve and the first discharge valve) or different discharge valves (for example, the first discharge valve and the second discharge valve). More preferably, the intermittent opening/closing is done by using the same discharge valve.

Figure 3B:
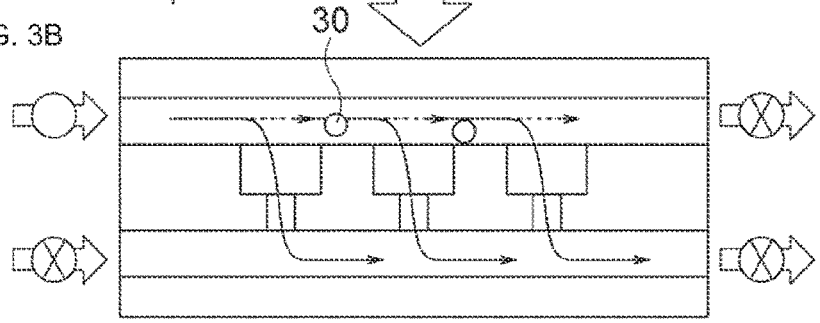
Figure 3C:
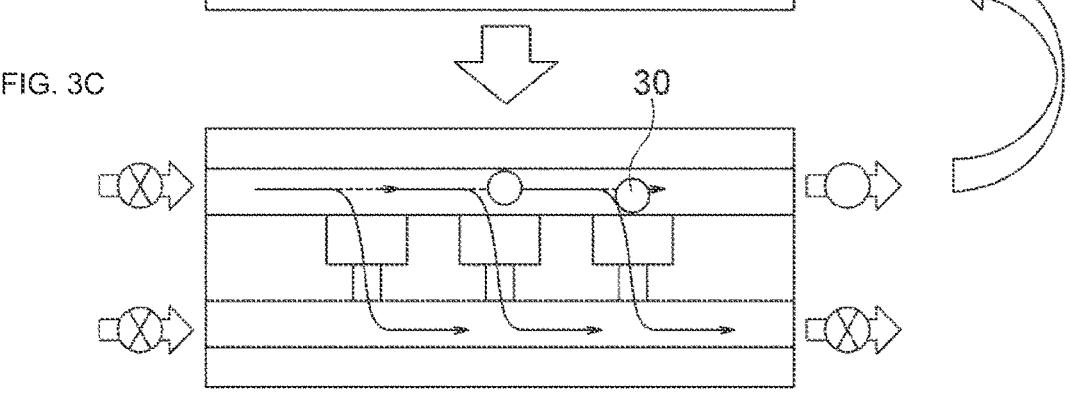

Note that, as illustrated in FIGS. 3A, 3B, and 3C, the fluid is allowed to move toward the first discharge valve 52 by the pressurizing step and the opening/closing step as described above, and is also allowed to move toward the second discharge valve 62 through a well/through hole region 9.

Performing such pressurizing step and the valve opening/closing step can discharge bubbles out of the chamber more efficiently.

In the valve opening/closing step, it is preferable to repeatedly perform the opening/closing of a supply valve for applying a positive pressure followed by the intermittent opening/closing of a discharge valve. More specifically, for example, a supply valve is opened to apply a positive pressure to a fluid in the chamber so that a bubble contracts, and then the supply valve is closed, and then a discharge valve is opened and closed intermittently so that the bubble expands and contracts repeatedly to move toward the discharge valve. As a result, a bubble in the chamber can be more efficiently moved toward the discharge side. Furthermore, a negative pressure may be applied to the discharge valve side by suction or the like to further facilitate the movement of the bubble toward the discharge side. Such intermittent opening/closing of a valve can cause bubbles to be discharged out of the chamber more efficiently.

Furthermore, in the bubble discharging method according to the first embodiment of the present technology, in a case where a bubble is present in the first space 3 or the first flow path 5, it is preferable to use first valves (the first supply valve 51 and the first discharge valve 52) connected to the first space 3 and a first flow path 5 to discharge the bubble. Furthermore, in a case where a bubble is present in the second space 4 or a second flow path 6, it is preferable to use second valves (the second supply valve 61 and the second discharge valve 62) connected to the second space 4 and the second flow path 6 to discharge the bubble.

Since a bubble in a fluid tends to rise in a direction opposite to the direction of the gravity, it is preferable to use a valve connected to the space and the flow path that are located on the upper side to discharge the bubble. For example, in a case where the first space is on the top side and the second space is on the bottom side, it is preferable to use the first valves connected to the first space and the first flow path to discharge a bubble. The method of the first embodiment is effective for a relatively small bubble present in the chamber.

Furthermore, the state of a bubble in the chamber may be observed by imaging the bubble. Observing a bubble ensures that the bubble discharging of the present technology is done efficiently throughout a time period until the bubble in the chamber is discharged. In addition, confirming that no bubble is present in the chamber by observing bubbles improves the efficiency and accuracy of, for example, trapping, analysis, and the like conducted in the particle trapping step, the particle analyzing step, and the like.

Furthermore, observation of bubbles makes it possible to determine in which space a bubble in the chamber is present, such as, in the first space and the first flow path or in the second space and the second flow path. For instance, as an example, on the basis of the location of a bubble on which the focus function or the like of the observation unit focuses, it can be determined in which location in the chamber, that is, the first space and the first flow path, the second space and the second flow path, or the like, the bubble is present. Moreover, it is preferable to observe bubbles from the viewpoint of efficiently discharging the bubbles on the basis of the result of observing the bubbles. It is preferable to further perform the bubble analyzing step of observing such bubbles in the chamber, determining the state of the bubbles, and the like.

As described above, according to the bubble discharging method of the first embodiment of the present technology, a bubble present in a fluid in the chamber can be efficiently discharged. Furthermore, in the case of the bubble discharging method of the first embodiment of the present technology, a fluid such as a buffer solution can be less consumed.

1-2. Bubble Discharging Method of Second Embodiment of the Present Technology The following describes a bubble discharging method according to a second embodiment of the present technology (see FIGS. 2, 4A, 4B, and 4C, for example). Description of any configuration overlapping the configuration of the above-described bubble discharging method of the present technology (such as the first embodiment) will be omitted as appropriate.

No specific limitation is imposed on the start of the bubble discharging method of the present technology as long as a fluid is present in the chamber.

In the second embodiment of the present technology, it is preferable to close all the valves 51, 52, 61, and 62 in the presence of a fluid in the chamber (see FIG. 4A, for example). Then, a supply valve is opened for the purpose of applying a positive pressure, and in the state where the valves other than this supply valve are closed, the fluid in the chamber is pressurized (see FIG. 4B: pressurizing step). Applying a positive pressure causes a bubble 30 in the chamber to contract into a smaller bubble or to dissolve in the fluid.

Note that a supply valve connected to the space where the bubble 30 is present is preferably used for applying a positive pressure. For example, in a case where the bubble 30 is present in the first space 3, the first supply valve 51 is preferably used, and in a case where the bubble is present in the second space 4, the second supply valve 61 is preferably used. In addition, in a case where the first space 3 is located on the upper side, the first supply valve 51 is preferably used because the bubble 30 tends to float.

Then, in the valve opening/closing step, while the supply valve for applying a positive pressure is open, at least one of the discharge valves is opened. While the supply valve is open, a positive pressure is applied into the chamber from a pump or the like, and when a valve is opened in the state where a positive pressure is being applied, a bubble in the chamber can be instantaneously removed. The method of the second embodiment can deal with various bubbles, and is more effective in discharging a relatively large bubble or a large number of bubbles in various sizes out of the chamber at a time. From the viewpoint of the consumed amount of a liquid such as a buffer solution, the second embodiment is preferably used when the size of a bubble is relatively large.

Here, it is preferable to open a discharge valve connected to the space (the first space or the second space) connected to the supply valve that has been used for applying a positive pressure, thereby moving a bubble more efficiently. For example, the first discharge valve 52 is preferably opened in the case of the first supply valve 51, and the second discharge valve 62 is preferably opened in the case of the second supply valve 61.

Note that, as illustrated in FIGS. 4A, 4B, and 4C, the fluid is allowed to move toward the first discharge valve 52 by the pressurizing step and the opening/closing step as described above, and is also allowed to move toward the second discharge valve 62 through the well/through hole region 9.

Furthermore, in the bubble discharging method according to the second embodiment of the present technology, in a case where a bubble is present in the first space 3 or the first flow path 5, it is preferable to use first valves (the first supply valve 51 and the first discharge valve 52) connected to the first space 3 and the first flow path 5 to discharge the bubble. Furthermore, in a case where a bubble is present in the second space 4 or the second flow path 6, it is preferable to use second valves (the second supply valve 61 and the second discharge valve 62) connected to the second space 4 and the second flow path 6 to discharge the bubble.

Since a bubble in a fluid tends to rise in a direction opposite to the direction of the gravity, it is preferable to use a valve connected to the space and the flow path that are located on the upper side to discharge the bubble. For example, in a case where the first space is on the top side and the second space is on the bottom side, it is preferable to use the first valves connected to the first space and the first flow path to discharge a bubble.

Furthermore, as with the above-described bubble discharging method of the first embodiment of the present technology, the state of a bubble in the chamber may be observed by imaging the bubble. Observing a bubble ensures that the method is carried out efficiently throughout a time period until the bubble in the chamber is discharged.

As described above, according to the bubble discharging method of the second embodiment of the present technology, a bubble present in a fluid in the chamber can be efficiently discharged. Furthermore, the bubble discharging method of the second embodiment of the present technology makes it possible to discharge, at a time, those bubbles that are relatively large in size, or are adhering on a wall or dispersed over the observed surface, that is, those bubbles that are difficult to discharge because, for example, a large number of bubbles are present.

Note that, in order to discharge bubbles in the chamber, the bubble discharging method of the first embodiment of the present technology and the bubble discharging method of the second embodiment may be appropriately combined in accordance with the state of bubbles or the like, or these methods may be alternately carried out.

1-3. Bubble Discharging Method of Third Embodiment of the Present Technology In a third embodiment, a bubble is discharged by using a microchip formed such that the upper side of the first space is gradually higher in the discharge direction (see FIG. 5, for example). For discharging a bubble, it is preferable to perform the pressurizing step and the valve opening/closing step, and in this case, it is more preferable to employ the bubble discharging method of the first embodiment of the present technology described above and/or the second bubble discharging method as appropriate.

Figure 5:
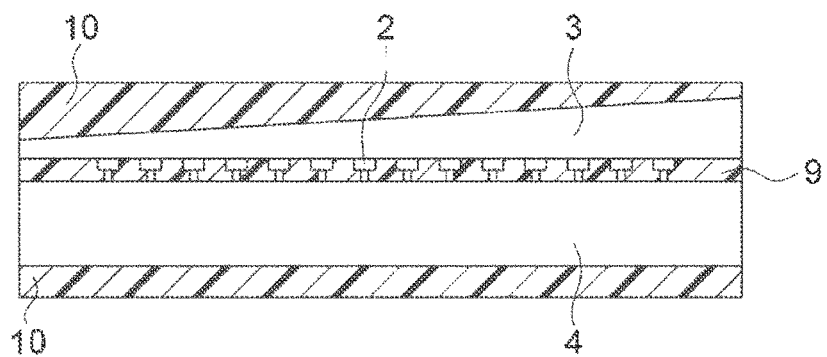
FIG. 5 is a diagram illustrating a modification of the microchip used for the bubble discharging method according to the present technology.
Figure 6A:
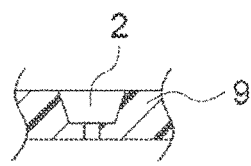
FIGS. 6A, 6B, 6C, 6D, and 6E are diagrams illustrating examples of a well or a through hole in a well/through hole region disposed in the chamber according to the present technology.
Figure 6D:
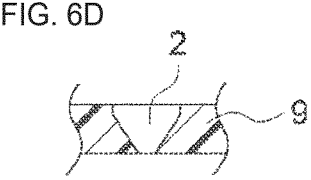
Figure 6B:
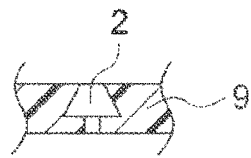
Figure 6E:
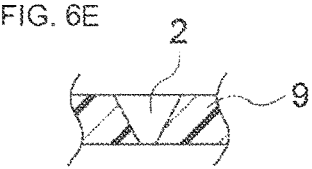
Figure 6C:
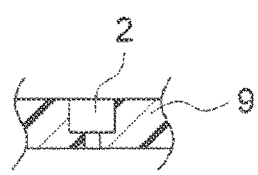

FIG. 5 shows an example of the microchip used in the third embodiment of the present technology, but the present technology is not limited thereto. As illustrated in FIG. 5, in a chamber including a microchip 10 that includes at least one well 2 or through hole to divide a space into the first space 3 and the second space 4, the microchip 10 is formed such that the upper side of the first space 3 is gradually higher in the discharge direction.

The following shows an example of the bubble discharging method of the present technology employing the microchip of the third embodiment of the present technology, but the present technology is not limited thereto.

The pressurizing step and the valve opening/closing step are performed according to the first embodiment or second embodiment described above, by using the microchip formed such that the upper side of the first space is gradually higher in the discharge direction and the cross-sectional area of the microchip across the width direction is gradually larger in the discharge direction. As a result, bubbles present in the fluid in the chamber can be efficiently discharged.

By employing a configuration in which a cross-sectional area is intentionally made gradually larger in the direction toward the outlet as described above, the flow velocity in the chamber can be reduced. On the other hand, if the flow velocity in the chamber is desired to be kept constant, a configuration in which the microchip has a constant cross-sectional area may be employed.

Examples of having a constant cross-sectional area may include: gradually decreasing the width of the microchip in the direction toward the outlet to compensate for the increased height in the direction toward the outlet; or making the microchip in a trapezoidal shape or the like by increasing the height near the center of the microchip and decreasing the height on the left and right sides.

1-4. Other Embodiments Employing Bubble Discharging Method of the Present Technology <Particle Trapping Method and Particle Analyzing Method of the Present Technology>

The bubble discharging method of the present technology can be applied, as appropriate, to an apparatus provided with a chamber and to a method carried out with the apparatus. In addition, since the present technology permits particles to be included in a fluid, the present technology can be used for particle trapping and particle analysis. The bubble discharging method of the present technology can be suitably incorporated into, for example, a particle trapping method or a particle analyzing method carried out with a chamber, but the bubble discharging method is not limited thereto.

The bubble discharging method of the present technology may be carried out as, for example, a pretreatment step in a particle trapping method or a particle analyzing method. In addition, the bubble discharging method of the present technology may be appropriately carried out in parallel with, or in the middle of, a particle trapping method or a particle analyzing method, as needed. Since bubbles may be entrained or remain in the middle of a step in a particle trapping method or a particle analyzing method, such bubbles can be discharged by using the bubble discharging method of the present technology.

As described above, the present technology can also provide a particle trapping method including the bubble discharging method of the present technology, or a particle analyzing method including the bubble discharging method of the present technology. In addition, the present technology can also provide a particle trapping apparatus or a particle analyzing apparatus having a configuration enabling the bubble discharging method of the present technology to be carried out.

In the present technology, the microchip is preferably a particle trapping chip that has a particle trapping region including at least one well or through hole. Furthermore, the particle is preferably a single cell. By using the bubble discharging method of the present technology, bubbles present in a fluid in the chamber can be efficiently discharged, and thus a particle (a single cell, for example) can also be trapped easily. In addition, in the present technology, it is preferable to perform a particle analyzing step of conducting an analysis relating to a particle.

The "particles" are preferably those which are required to be trapped or analyzed one by one, for example. Examples of the particles include, but are not limited to, biological microparticles such as cells, microorganisms, solid components derived from organisms, and liposomes, and synthetic particles such as latex particles, gel particles, and industrial particles. The cells may include animal cells and plant cells. Examples of the animal cells may include tumor cells and blood cells. The microorganisms may include bacteria such as *Escherichia coli* and fungi such as yeast. Examples of the solid components derived from organisms may include solid crystals produced in an organism. The synthetic particles may be, for example, particles including an organic or inorganic polymer material, a metal, or the like. The organic polymer materials may include polystyrene, styrene-divinylbenzene, polymethyl methacrylate, and the like. The inorganic polymer materials may include glass, silica, magnetic materials, and the like. The metals may include gold colloid, aluminum, and the like. Furthermore, in the present technology, the particle may be a combination of a plurality of particles such as two or three particles.

The particle trapping method and the particle analyzing method of the present technology are not particularly limited as long as the methods can be carried out with any of various particle trapping apparatuses, particle analyzing apparatuses, and the like that can use the chamber of the present technology described above.

The following shows Example 1 and Example 2 of the particle trapping method and the particle analyzing method; however, the methods are not limited to these examples, and the bubble discharging method of the present technology can be used for general particle trapping methods and particle analyzing methods.

Figure 7:
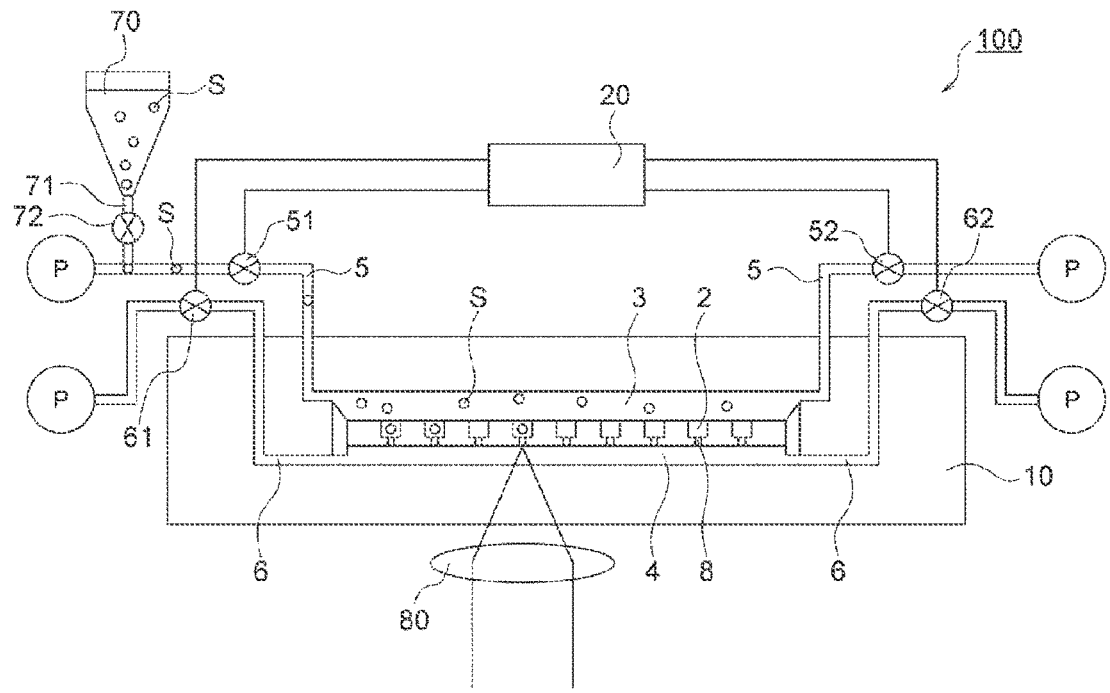
FIG. 7 is a diagram showing a conceptual diagram of a particle trapping apparatus or a particle analyzing apparatus according to the present technology.

1-4 (A) Example 1 of Particle Trapping Method and Particle Analyzing Method of the Present Technology Referring to the apparatus illustrated in FIG. 7, the following describes an example of a particle trapping method and a particle analyzing method used in the present technology, but the method and apparatus of the present technology are not limited to this example.

For example, in an example of the particle trapping method of the present technology, the particle trapping step, the step of removing particles that were not trapped, the step of analyzing the trapped particles, the step of taking a desired particle from the trapped particles, and the step of collecting other trapped particles are performed; however, the present technology is not limited thereto.

In step S100, the above-described bubble discharging method of the present technology (more preferably, the first to third embodiments) may be carried out as a pretreatment in the particle trapping method or the particle analyzing method. As a result, bubbles present in the fluid in the chamber can be efficiently discharged. Then, the particle trapping and particle analysis are started from step S101.

In step S101, the particle trapping method used in the present technology is started. Prior to the start of the particle trapping method, a fluid containing particles S is poured into a container 70.

In step S102, the particle trapping step is performed. Prior to supply or suction of particles, a particle supply valve 72 connected to a particle flow path 71 disposed between the first flow path 5 and the container 70 may be closed. Opening/closing of the particle supply valve 72 can be appropriately regulated in accordance with the state of supply of particles to the first space 3. The particle supply valve 72 can regulate supply of particles. In the particle trapping step, the particle supply valve 72 connected to the particle flow path 71 is opened, and then the pump (P in the figure) on the first supply valve 51 side or on the first discharge valve 52 side starts supply or suction of particles. When the supply or suction is started, the supply or suction causes the fluid containing the particles S to enter the first flow path 5 via the first supply valve 51 from the container 70. Opening/closing the first supply valve 51 and the first discharge valve 52 controls the flow rate, flow velocity, and the like of the fluid. The fluid containing the particles S passes through the first flow path 5 and enters the first space 3 in a particle trapping chamber 100. The supply or suction of the fluid is further continued by a pump so that the particles S enter a well 2 by their own weight or sedimentation. Having entered the well 2, the particles S hit against the entrance of a hole 8, where the particles S stop moving. In this way, particles are trapped in the well 2.

In step S103, the step of removing particles S that have not been trapped in the well is performed. In the removal step, the particles S that have not been trapped in the well may be discharged from the particle trapping chamber 100. The particles S that have not been trapped in the well can be drawn by the pump connected to the first discharge valve 52 so as to be discharged via the first flow path 5 and the first discharge valve 52.

In step S104, the step of analyzing the particles trapped in the well is performed. In the analyzing step, for example, an observation under an inverted microscope 80 may be made. In addition, in the analyzing step, an analysis may be conducted with an analysis apparatus other than the inverted microscope. For example, in the analyzing step, an analysis of fluorescence emitted by each particle may be conducted with a photodetector.

In step S105, the step of taking a desired particle from the trapped particles is performed. In the taking step, first, a desired particle is selected as a result of the analysis in step S104. For example, a particle having a desired shape or a particle emitting desired fluorescence may be selected. Then, the selected particle is taken by a single particle taking apparatus such as a micromanipulator, for example.

In step S106, the step of collecting the other trapped particles, that is, the particles that have not been selected in step S105, is performed. First, the first discharge valve 52 is opened, and then the pump connected thereto applies a pressure (a positive pressure, for example) so that the particles S come out of the well 2. The particles S that have come out of the well 2 pass through the first flow path 5 on the first discharge valve 52 side to be collected in a container (not illustrated).

In step S107, the particle trapping method of the present technology is ended.

As a result of the flow described above, particles can be observed one by one. In addition, a single particle of interest can be taken. Furthermore, the other particles trapped in the well and the particles that have not been trapped in the well can be collected and used for another test. Alternatively, the flow described above may employ a particle trapping chamber that includes through holes instead of wells.

Note that, if a bubble is present in the chamber during the steps S101 to S107 described above, the bubble discharging method of the present technology may be carried out as appropriate. Thus, a bubble can be discharged from the chamber as appropriate. Preferably, the method is carried out immediately before the particle trapping step of step S102 to discharge bubbles, thereby increasing the number of particles that can be fractionated and trapped. In addition, preferably, the method is carried out immediately before the particle analyzing step of step S104 to discharge bubbles, thereby further improving the contrast and the like of an image or the like obtained by imaging a particle and the accuracy of particle counting.

Figure 8:
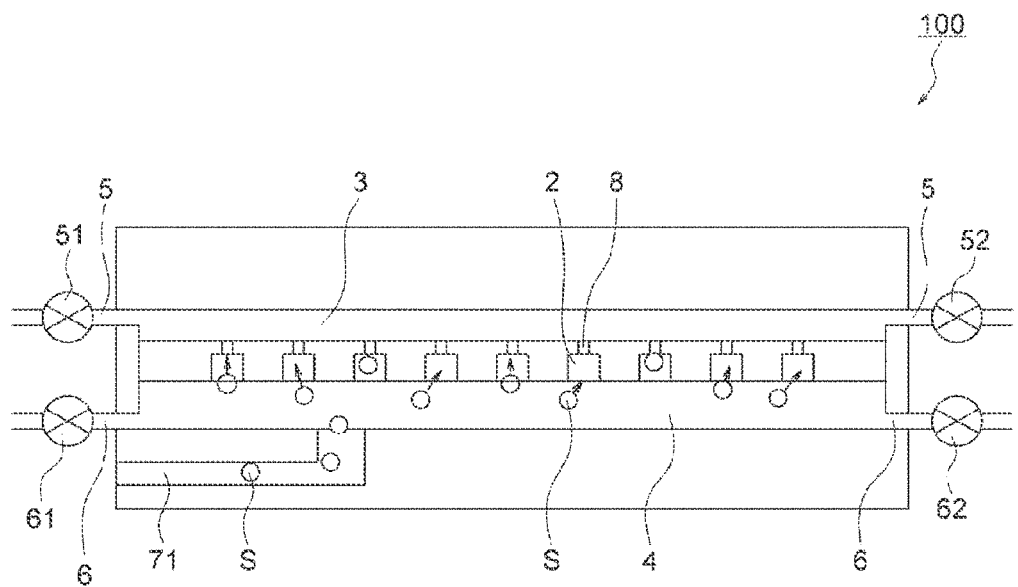
FIG. 8 is a diagram illustrating a modification of the chamber according to the present technology.

1-4 (B) Example 2 of Particle Trapping Method and Particle Analyzing Method of the Present Technology Referring to the apparatus illustrated in FIG. 8, the following describes an example of a particle trapping method and a particle analyzing method used in the present technology, but the method and apparatus of the present technology are not limited to this example. The bubble discharging method of the present technology can also be applied to a chamber in which an opening for trapping particles is facing downward and particles are trapped by suction, as illustrated in FIG. 8. Description of components overlapping those in Example 1 above will be omitted as appropriate.

In step S200, the above-described bubble discharging method of the present technology (more preferably, the first to third embodiments) may be carried out as a pretreatment in the particle trapping method or the particle analyzing method. As a result, bubbles present in the fluid in the chamber can be efficiently discharged. Then, the particle trapping and particle analysis are started from step S201.

In step S201, the particle trapping method used in the present technology is started. Prior to the start of the particle trapping method, a fluid containing particles is poured into a container (not illustrated).

In step S202, the particle trapping step is performed. Prior to suction of particles, the valves 51, 52, 61, and 62 may be closed. In the particle trapping step, the first supply valve 51 or the first discharge valve 52 is opened, and then the pump (P in the figure) connected to either of the valves starts suction of particles. When the suction is started, the fluid containing the particles S passes through the particle flow path 71 from the container and enters the second space 4 on the sedimentation side of the particle trapping chamber 100. The suction is further continued so that the particles S float in the second space 4 on the sedimentation side and enter the well 2. Having entered the well 2, the particles S hit against the entrance of a hole 8, where the particles S stop moving. In this way, particles S are trapped in the well 2. In the particle trapping step, the suction is stopped or the suction force is reduced after a predetermined time has elapsed from the start of the suction. As a result, the particles stop floating in the chamber, and the particles that have not been trapped in the well settle on the bottom surface of the chamber.

In step S203, the step of removing particles that have not been trapped in the well is performed. In the removal step, the particles that have not been trapped in the well may be discharged from the particle trapping chamber 100. For example, the particles are drawn by the pump connected to the particle flow path 71, whereby the particles settled on the bottom surface of the chamber may be discharged from the chamber 100 via the particle flow path 71 and collected in a container (not illustrated).

In step S204, the step of analyzing the particles trapped in the well is performed.

In step S205, the step of taking a desired particle from the trapped particles is performed. Steps S204 and S205 may be similar to steps S104 and S105 described above, and thus description thereof is omitted.

In step S206, the step of collecting the other trapped particles, that is, the particles that have not been selected in step S205, is performed. First, the first supply valve 51 or the first discharge valve 52 is opened, and the pump connected thereto applies a pressure (a positive pressure, for example) so that the particles come out of the well. The particles that have come out of the well pass through the particle flow path 71 and may be collected in a collecting container (not illustrated).

In step S207, the particle trapping method of the present technology is ended.

As a result of the flow described above, particles can be observed one by one. In addition, a single particle of interest can be taken. Furthermore, the other particles trapped in the well and the particles that have not been trapped in the well can be collected and used for another test. Alternatively, the flow described above may employ a particle trapping chamber that includes through holes instead of wells.

Note that, if a bubble is present in the chamber during the steps S201 to S207 described above, the bubble discharging method of the present technology may be carried out as appropriate. Thus, a bubble can be discharged from the chamber as appropriate. Preferably, the method is carried out immediately before the particle trapping step of step S202 to discharge bubbles, thereby increasing the number of particles that can be fractionated and trapped. In addition, preferably, the method is carried out immediately before the particle analyzing step of step S204 to discharge bubbles, thereby further improving the contrast and the like of an image or the like obtained by imaging a particle and the accuracy of particle counting.

With regard to the present technology, those skilled in the art understand that various modifications, combinations, sub-combinations, or alternatives can be made in accordance with, for example, design requests, other factors, or the like within the scope of the present technology and its equivalents.

1-5. Examples 1 to 3 of Bubble Discharging Method of the Present Technology

The present technology will now be described in more detail on the basis of examples and the like. Note that the examples and the like described below show an example of representative examples or the like of the present technology, and the scope of the present technology is not construed as being limited by the examples.

[Basic Configuration]

Figure 2:
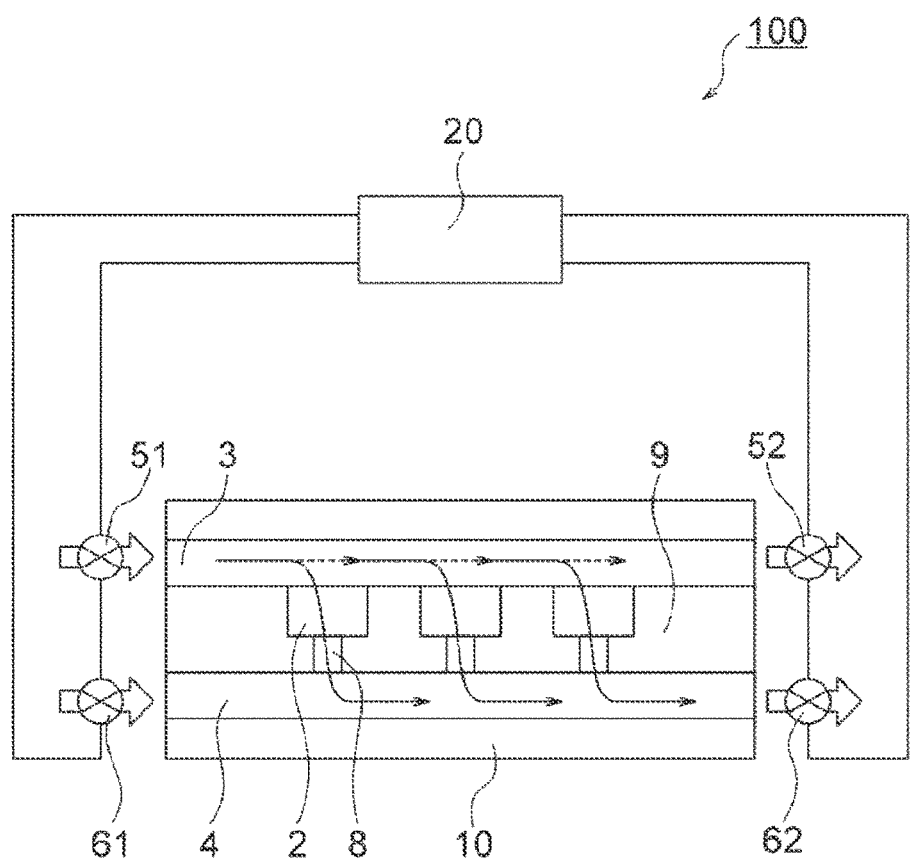
FIG. 2 is a schematic diagram illustrating a bubble discharge system and a bubble discharging method according to the present technology.

In a mode for implementing the present disclosure, it is assumed that, as illustrated in the overall configuration diagrams in FIGS. 1 and 2, the microwell arrayed in a mesh, the valves 51, 52, 61, and 62 allowed to open and close at the inlets and outlets of the upper flow path and the lower flow path provided so as to vertically sandwich the well array, and a pressure control unit 20 beyond the valves are disposed. In this mode, a positive pressure and a negative pressure are controlled by the pressure control unit 20 and entrained bubbles are discharged by operating the individual valves.

Figure 10:
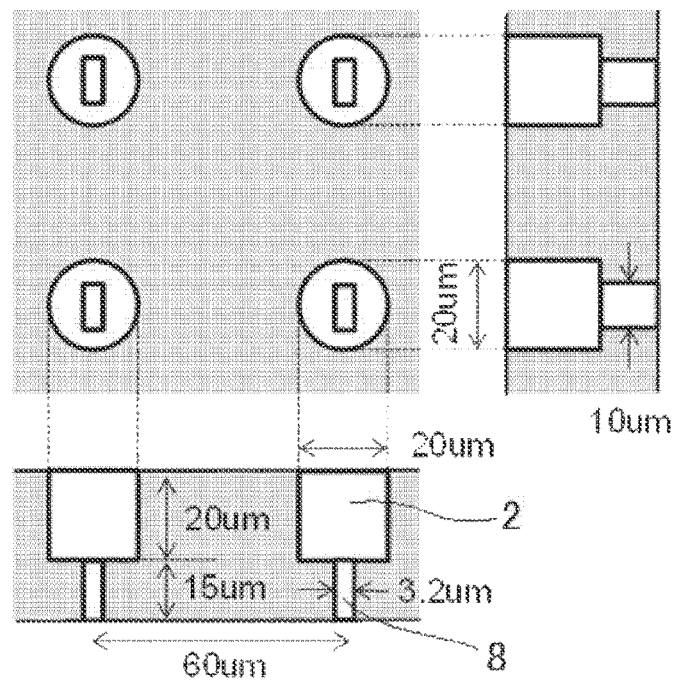
FIG. 10 is a schematic diagram illustrating an example of wells disposed in a particle trapping chamber of the present technology.

Microwell array (see FIG. 10)

Assuming that cells are φ10 to 20 μm in diameter, the microwell is designed in accordance with, for example, the following specifications.

Microwell: φ20 μm×depth 20 μm

Fine through hole: slit-shaped/width 3.2 μm×length 10 μm×depth 15 μm

Substrate material: glass/plastic resin such as acrylic or polystyrene/rubber such as PDMS Well pitch: 60 μm each in X and Y directions The number of wells: 7,000 or less Microwell area dimensions: X direction 8 mm×Y direction 8 mm These numerical values are not restrictive but may optimized in any way depending on the purpose and cell type.

The following describes examples in which entrained bubbles are removed by using the first supply valve 51 (upper IN valve) and the first discharge valve 52 (upper OUT valve) in a case where a bubble is entrained into the upper flow path, while entrained bubbles are removed by using the second supply valve 61 (lower IN valve) and the second discharge valve 62 (lower OUT valve) in a case where a bubble is entrained into the lower flow path.

EXAMPLE 1

Example 1 is described below with reference to FIGS. 3A, 3B, and 3C. In a case where a bubble is entrained during priming with a buffer solution or the like (FIG. 3A), the first supply valve 51 (the upper IN valve) is opened and a positive pressure up to about +Δ300 hPa is applied. Then, the entrained bubble 30 contracts as in (FIG. 3B). In this state, when the first supply valve 51 (the upper IN valve) is closed and the first discharge valve 52 (the upper OUT valve) is opened, the entrained bubble slightly moves toward the outlet side as in (FIG. 3C). At the same time, a negative pressure may be applied to the first discharge valve (the upper OUT valve) side to facilitate the movement toward the outlet. Performing the operations in (FIG. 3B) and (FIG. 3C) repeatedly allows the entrained bubble 30 to move to the outlet. In the case of this method, a buffer solution or the like can be less consumed.

EXAMPLE 2

Example 2 is described below with reference to FIGS. 4A, 4B, and 4C. As in Example 1, in a case where a bubble is entrained during priming with a buffer solution or the like (FIG. 4A), the first supply valve 51 (the upper IN valve) is opened and a positive pressure up to about +Δ300 hPa is applied. Then, the entrained bubble 30 contracts as in (FIG. 4B). Then, when the first discharge valve (the upper OUT valve) is opened while the first supply valve 51 (the upper IN valve) is kept open and a positive pressure is applied, the entrained bubble 30 moves toward the outlet with momentum as in (FIG. 3C). At the same time, a negative pressure may be applied to the first discharge valve 52 (the upper OUT valve) side to further facilitate the movement toward the outlet. In the case of this method, the entrained bubble can be removed instantaneously as compared with Example 1.

EXAMPLE 3 APPLICATION EXAMPLE

Because of the tendency of bubbles to travel in a direction opposite to their own weight, bubbles are often entrained into the upper flow path over the well array. Therefore, as illustrated in FIG. 5, the upper side (ceiling) of the upper flow path is made gradually higher toward the outlet of the first discharge valve 52 (the upper OUT valve) so that bubbles are guided to the outlet. Specifically, bubbles successfully move toward the outlet in practice by providing the upper flow path having a height of 0.1 mm and a width of 0.7 mm or less on the first supply valve 51 (the upper IN valve) side, and a height of 0.3 mm and a width of 1.5 mm or less on the first discharge valve 52 (the upper OUT valve) side. With the upper flow path in such form and valve operations, entrained bubbles can be discharged with a higher probability.

In the present application example, the flow velocity is designed to gradually decrease by intentionally increasing the cross-sectional area toward the outlet. However, the flow velocity can be kept constant by, for example, 1) decreasing the width to compensate for the increased height; or 2) increasing the height only in the center and decreasing the height on the left and right sides into a trapezoidal shape, so that the cross-sectional area is kept constant.

Furthermore, a small bubble can possibly be dissolved in the liquid only by applying a positive pressure. Therefore, it may be easy to conceive a system capable of determining, through imaging or the like, the presence or absence of a bubble and the size of a bubble to automatically select 1) application of a positive pressure only, or 2) application of a positive pressure plus valve operations.

2. Apparatus According to the Present Technology 2-1. Apparatus Including Chamber and Pressure Control Unit According to the Present Technology An apparatus according to the present technology may be a bubble discharging apparatus that is configured to carry out the bubble discharging method of the present technology as described above and is intended to discharge bubbles in the chamber.

The apparatus according to the present technology is preferably an apparatus that includes a chamber and a pressure control unit. The chamber preferably includes a microchip that at least includes one well or one through hole to divide a space into a first space and a second space. The pressure control unit preferably exerts control so that the pressurizing step of applying a positive pressure to a fluid in the chamber and the valve opening/closing step are performed to discharge bubbles in the chamber. In addition, the pressure control unit is capable of operating the valves for opening/closing a first flow path connected to the first space and/or a second flow path connected to the second space by performing the valve opening/closing step.

In addition, some or all of the functions fulfilled by the pressure control unit may be disposed outside the apparatus according to the present technology or may be disposed in an accessible information processing apparatus (for example, a server or the like). Furthermore, the pressure control unit of the present technology may work in cooperation with another control unit or a central control unit, or may be incorporated in another control unit or a central control unit.

According to the present technology, a pressure control apparatus, a valve, a pump, an observation apparatus, an analysis apparatus, and the like can be included as appropriate and on an as-needed basis. The observation apparatus is capable of observing the location, the size, and the like of a bubble in the chamber. In addition, the analysis apparatus is capable of conducting analysis such as bubble analysis and particle analysis as appropriate.

Furthermore, the apparatus of the present technology may be a particle trapping apparatus that includes a bubble discharging apparatus capable of carrying out the method of the present technology and that traps a particle into the well or through hole. Furthermore, the apparatus of the present technology may be a particle analyzing apparatus that analyzes particles and includes a bubble discharging apparatus capable of carrying out the method of the present technology.

Note that description about configurations and steps related to the apparatus according to the present technology and operations of the apparatus overlapping the above-described configurations and steps is omitted as appropriate.

The chamber in the apparatus according to the present technology is preferably a structure provided with a space for moving a fluid or a fluid containing particles. In addition, the chamber of the present technology may employ a configuration that includes a microchip having at least one well or through hole. Furthermore, the present technology may employ a configuration in which the microchip has a well or through hole to divide a space into the first space and the second space, or may employ a configuration in which the chamber includes such microchip.

In a configuration according to the present technology, at least one well or at least one through hole is included to separate a space into a first space and a second space (see FIG. 1, for example). In the present technology, it is preferable that a region at least having one well or one through hole is included.

In addition, in the present technology, each of the first space and the second space may be either a flow path along which a fluid or a fluid containing particles can move as appropriate or a portion including the flow path. Furthermore, in the present technology, a first flow path connected to the first space and/or a second flow path connected to the second space is included.

Furthermore, in the present technology, it is preferable that a valve for opening/closing the first flow path connected to the first space and a valve for opening/closing the second flow path connected to the second space are included. Furthermore, in the present technology, it is preferable that a valve for opening/closing either one or both of the first flow path connected to the first space and the second flow path connected to the second space is included.

For the discharge of bubbles according to the present technology, a valve is not limited to a specific type and those skilled in the art may select a valve as appropriate. As the valves, commercially available ones can be used.

In addition, for the discharge of bubbles according to the present technology, one or more valves may be used; however, the number of valves is preferably two or more because of ease of controlling the discharge of bubbles. Moreover, it is preferable to connect two valves to each of the supply side and the discharge side of a flow path.

Note that, in the present technology, the means for sedimentation of particles is not particularly limited, and examples thereof include gravity, centrifugal force, suction, pushing, and the like. Furthermore, the means for floating of particles is not particularly limited, and examples thereof include suction, pushing, and the like. For example, a component (for example, a pump or the like) that draws or pushes a fluid in the flow path may be included, and particles may be moved into a well or through hole by suction or pushing.

Furthermore, in the present technology, the suction or pushing may be done by any means known to those skilled in the art such as, for example, by a pump. As the pump, commercially available one may be used. The pump is not limited to a specific type and an appropriate pump may be selected by those skilled in the art in accordance with, for example, the suction force, pushing force, or the like to be applied.

2-2. Chamber and Microchip According to the Present Technology

The following describes preferred implementations of the chamber or microchip of the present technology.

In the chamber or microchip of the present technology, a hole may be disposed in the well (see FIGS. 6A, 6B, 6C, 6D, and 6E, for example). Via the hole, the well can communicate with the first flow path and/or the second flow path. That is, the hole passes through the well region from the well side to the first flow path side and/or the second flow path side. Suction takes place through the hole and via the first flow path and/or the second flow path, whereby particles can be transferred into the well. The number of holes disposed in each well may be, for example, 1 to 10, particularly 1 to 5, and more particularly 1 to 3. From the viewpoint of ease of manufacture, the number of holes disposed in each well may be one or two, particularly one.

In the chamber or microchip of the present technology, any shape may be employed as the shape of the entrance of the hole. In the present technology, the entrance of the hole refers to an opening portion of the hole on the well wall in which the hole is disposed. The shape of the entrance of the hole may be, for example, circular, elliptical, polygonal, such as triangular, quadrangular (for example, rectangle, square, parallelogram, and rhomboid), pentagonal, hexagonal, or the like (see FIGS. 4A, 4B, and 4C, for example). In the present technology, the shape of the entrance of the hole may be preferably quadrangular, more preferably rectangular or square, and still more preferably rectangular.

In the chamber or microchip of the present technology, it is desirable that the entrance of the hole may have dimensions that prevent a particle contained in a fluid from passing through the hole by suction and traveling to the other flow path side. For example, the minimum dimensions of the entrance of the hole are less than the dimensions of a particle.

For example, in a case where the shape of the entrance of the hole is rectangular, the shorter side or the longer side of the rectangle, particularly the shorter side of the rectangle, may have a dimension smaller than the dimensions of a particle contained in a fluid (for example, the diameter of a particle or the like). For example, the length of the shorter side of the rectangle is not particularly limited as long as it is set so as not to interfere with suction. For example, the length of the shorter side of the rectangle may be 0.01 times to 0.9 times the dimensions of a particle contained in a fluid (for example, the diameter of a particle). Such shape of the hole makes it possible to trap a particle while suppressing damage to the particle.

In the chamber or microchip of the present technology, the shape of the entrance of the hole is preferably rectangular. The length of the longer side of the rectangle is preferably 1.2 times to 5 times the length of the shorter side of the rectangle. Such slit shape can suppress damage to a particle when the particle is trapped in the well. Such slit shape is particularly preferable in a case where the particle is a cell. The entrance of the hole has a slit shape, which can suppress damage to cells while preventing the cells from passing through the hole. For example, the entrance of the hole may be in a slit shape with the shorter side being 1 μm to 10 μm, particularly 2 μm to 8 μm and the longer side being 5 μm to 20 μm, particularly 6 μm to 18 μm.

In the chamber or microchip of the present technology, the hole may preferably be disposed at the bottom of the well. The hole disposed at the bottom of the well has a shorter length than the hole disposed on a side surface of the well. As a result, the manufacture may be easier. The bottom of the well may be, for example, one of the walls included in the well, the one being on the side opposite to the entrance of the well.

From the viewpoint of workability, the hole preferably has a shallower depth. On the other hand, from the viewpoint of strength in trapping a particle, the hole preferably has a greater depth. Therefore, in a case where the hole is disposed at the bottom of the well in the present technology, the depth of the hole (that is, the distance from the bottom surface of the well to the surface opposite to the particle trapping surface) may be preferably 5 to 100 μm, more preferably 6 to 50 μm, and even more preferably 10 to 30 μm.

Note that the "particle trapping surface" in the present technology refers to a surface through which a particle moving along a flow path enters the well or the through hole. Furthermore, in the present technology, the surface provided with the well or the surface provided with the through hole is also referred to as a "particle trapping surface".

In the chamber or microchip of the present technology, the well may be opened in a direction to the first space or to the second space, the orientation of the entrance of the well is not particularly limited, and the opening is preferably provided in the particle trapping surface. For example, in a case where particles are caused to settle by their own weight, by suction, or the like to be trapped, the entrance of the well may face the side opposite to the side on which the particles will settle, whereby particles moving in the chamber can be trapped in the well by their own weight, by suction, or the like. On the other hand, in a case where particles are trapped by a force acting in a direction opposite to sedimentation, it is preferable that, for example, the entrance of the well faces the side on which particles will settle, whereby particles moving in the chamber can be trapped in the well by suction in a direction opposite to the direction in which particles will settle.

In the chamber or microchip of the present technology, each of the wells may have a shape that allows a single particle to be trapped (see FIGS. 6A, 6B, 6C, 6D, and 6E, for example). For example, the entrance of the well may be in a shape such as, for example, circular, elliptical, polygonal, such as triangular, quadrangular (for example, rectangle, square, parallelogram, and rhomboid), pentagonal, hexagonal, and the like. In the present technology, the entrance of the well refers to an entrance portion of the well on a surface on which the well for trapping particles is disposed. The shape of the entrance of the well may be designed, for example, such that a particle to be trapped can enter the well but a particle that should not be trapped cannot enter the well.

In another implementation, the well may be in a shape that has the smallest cross-sectional area at the entrance of the well and a larger cross-sectional area in the inside of the well. Such shape may prevent particles that have entered the well from leaving the well.

In still another implementation, the well may be in a shape that has the largest cross-sectional area at the entrance of the well and a smaller cross-sectional area in the inside of the well. Such shape may allow particles to enter the well more easily.

In the chamber or microchip of the present technology, a through hole plays a role similar to that of the above-described hole. All the description about the hole applies to the through hole. For example, the description about the shape and dimensions of the entrance of the above-described hole applies to the description about the two openings (in particular, out of the two openings, the opening to trap a particle) of the through hole.

In addition, the length of the through hole (that is, the distance between the two openings) may be the same as the thickness of the through hole region, and in particular, may be the same as the thickness of the plate-like portion, which is described below.

The shape of the through hole may be, for example, cylindrical, prismatic (for example, triangular prismatic or rectangular prismatic), or chevron-shaped, or may be any other shape.

For example, in a case where the shape of the through hole is rectangular prismatic, the opening of the through hole on the particle trapping surface may be in a rectangular shape and the rectangular shape may be continuous to the opposite surface.

Alternatively, in a case where the through hole is chevron-shaped, the lateral side (that is, the sloped side) of the through hole may be linear or curved (such as, for example, an arc-shaped side). In this case, a particle may be trapped near the opening of the through hole, or may be trapped in the middle of the through hole.

Furthermore, as another shape of the through hole, for example, the through hole may have a fixed shape from the opening on the particle trapping surface to the middle of the through hole, and from the middle thereof, the transverse cross-sectional area of the through hole may be gradually smaller. Examples of such shape may include the shape of a microneedle and the like.

The well region or the through hole region in the chamber or microchip of the present technology may have at least one surface provided with the well or the through hole. In the present technology, the surface provided with the well or the surface provided with the through hole so as to be capable of trapping a particle is also referred to as a particle trapping surface.

The particle trapping surface may be a flat surface or a curved surface. From the viewpoint of ease of manufacture, the particle trapping surface is preferably flat. In a case where the particle trapping surface is flat, the particle trapping surface may be disposed so that the flat surface is perpendicular to the direction of action of gravity on particles or the flat surface forms an angle of less than 90 degrees with the direction of action.

In the chamber or microchip of the present technology, the wells or the through holes may be regularly arranged on a surface for trapping particles. The regular arrangement of wells or through holes makes it easier to locate the well or through hole in which the particle of interest is trapped. As a result, for example, it is made possible to more easily take out and/or observe the particle trapped in the well or through hole. For example, the wells or the through holes may be arranged in a row or a plurality of rows at predetermined intervals on the particle trapping surface, or the wells or the through holes may be arranged in a grid pattern at predetermined intervals on the particle trapping surface. The interval may be appropriately selected by those skilled in the art in accordance with, for example, the number of particles to be given and the number of particles to be trapped. The interval can be, for example, 20 μm to 300 μm. For example, in a case where the wells or through holes are arranged in a grid pattern, the wells or through holes may be arranged at the intervals illustrated above along the X and Y directions on the particle trapping surface.

More preferably, in the chamber or microchip of the present technology, the well region or the through hole region may be disposed so as to divide the inside of the chamber into a first space and a second space. As a result of the division, the well/through hole region has surfaces in contact with the first space or the second space.

In the present technology, it is preferable that the well region or the through hole region is a particle trapping region and, in this case, the particle trapping region has at least one surface for trapping particles as a result of the division. More preferably, the microchip is a particle trapping chip that includes the particle trapping region.

In the chamber or microchip of the present technology, in a case where the particle trapping region includes the well or through hole, particles move in the chamber and can be trapped in the well by sedimentation or suction. The well or through hole in the region has an opening for trapping a particle and the direction of the opening is not particularly limited. The particle trapping region can be disposed in the chamber so as to allow for such movement and trapping of particles.

In the chamber or microchip of the present technology, the number of wells or through holes is not limited to any specific range, and the range may be, for example, 1 to 1,000,000, particularly 10 to 800,000, more particularly 100 to 600,000, and even more particularly 1,000 to 500,000.

In the present technology, the first space may be a flow path for flowing a fluid or a fluid containing particles, or may be a portion including the flow path. In addition, in the present technology, the second space may be a flow path for flowing a fluid or a fluid containing particles, or may be a portion including the flow path.

In the chamber or microchip of the present technology, the fluid or the fluid containing particles can move through the first space, the second space, the first flow path, and the second flow path. These spaces and flow paths are preferably configured to be used for trapping particles into the wells or through holes. The first space is preferably connected to the first flow path. The second space is preferably connected to the second flow path. As a result, suction can be done such that particles are trapped into the wells or through holes through the first flow path and/or the second flow path.

In the chamber or microchip of the present technology, the particle trapping region may be connected to a suction unit. The suction may be provided by the suction unit. The suction unit may be, for example, a pump known to those skilled in the art. The pump used in the present technology is preferably a pump capable of finely adjusting the suction force, and more preferably a pump capable of controlling a pressure in the order of several tens of Pa around 1 kPa. Such pump is commercially available and examples thereof may include KAL-200 (halstrup-walcher GmbH).

In the chamber or microchip of the present technology, the particle trapping region may be used not only when particles are trapped into the well or through hole but also when particles trapped in the well are discharged from the well or when particles trapped in the through hole are discharged from the through hole. For example, in a case where suction is provided with a negative pressure, the discharge may be done by applying a positive pressure.

The accuracy and efficiency of cell trapping and cell image analysis can be further improved by the combined effect of the chamber or microchip (for example, the configuration, structure, and the like thereof) of the present technology and the bubble discharging method of the present technology.

2-3. Particle Trapping Apparatus According to the Present Technology

Description about configurations and steps related to the particle trapping apparatus according to the present technology and operations of the apparatus overlapping the above-described configurations and steps is omitted as appropriate. In addition, description about configurations and the like overlapping the configurations and the like of Examples 1 and 2 of the apparatus according to the present technology as described later is also omitted as appropriate.

The particle trapping apparatus of the present technology is an apparatus provided with a chamber that includes a microchip that includes at least one well or through hole to divide a space into a first space and a second space. Furthermore, the particle trapping apparatus of the present technology is configured to discharge a bubble in the chamber by performing a pressurizing step of applying a positive pressure to a fluid in the chamber and a valve opening/closing step of operating a valve for opening/closing a first flow path connected to the first space and/or a second flow path connected to the second space. The particle trapping apparatus of the present technology further includes a control unit that controls the pressurizing step and the valve opening/closing step.

Moreover, the particle trapping apparatus according to the present technology is an apparatus configured to, in the chamber that includes the microchip that includes at least one well or through hole to divide a space into the first space and the second space, trap a particle into the well or through hole. Furthermore, it is preferable that the apparatus further includes an observation unit and an analysis unit, which are described later.

The microchip is preferably a particle trapping chip that has a particle trapping region including at least one well or through hole. Furthermore, the particle is preferably a single cell.

In the present technology, the pressure control unit allows bubbles present in a fluid in the chamber to be discharged efficiently. As a result, the accuracy, efficiency, and the like of particle trapping and the like can be improved. For example, while conventional technologies do not make it possible to fractionate and trap particles such as cells with regard to a region where a bubble is entrained, the present technology makes it possible to discharge entrained bubbles, thereby increasing the number of particles such as cells that can be fractionated and trapped.

Note that effects provided by the present technology are not necessarily limited to the effects described above, but may be any of the effects described herein.

2-4. Particle Analyzing Apparatus According to the Present Technology

Description about configurations and steps related to the particle analyzing apparatus according to the present technology and operations of the apparatus overlapping the above-described configurations and steps is omitted as appropriate. In addition, description about configurations and the like overlapping the configurations and the like of Examples 1 and 2 of the apparatus according to the present technology as described later is also omitted as appropriate.

The particle analyzing apparatus of the present technology is an apparatus provided with a chamber that includes a microchip that includes at least one well or through hole to divide a space into a first space and a second space. Furthermore, the particle analyzing apparatus of the present technology is configured to discharge a bubble in the chamber by performing a pressurizing step of applying a positive pressure to a fluid in the chamber and a valve opening/closing step of operating a valve for opening/closing a first flow path connected to the first space and/or a second flow path connected to the second space. The particle analyzing apparatus of the present technology includes a pressure control unit that controls the pressurizing step and the valve opening/closing step.

Furthermore, the particle analyzing apparatus according to the present technology includes: an observation unit that images a bubble in the chamber under a microscope; and an analysis unit that conducts an analysis of the bubble on the basis of information acquired from the observation unit. Additionally, or alternatively, the particle analyzing apparatus according to the present technology includes: an observation unit that images under a microscope a particle trapped in the well or through hole; and an analysis unit that conducts an analysis of the trapped particle on the basis of information acquired from the observation unit.

The bubble discharging method of the present technology may be carried out before or after particles are supplied into the chamber.

In the particle analyzing apparatus of the present technology, the pressure control unit, the analysis unit, and the like allow bubbles present in a fluid in the chamber to be discharged efficiently. As a result, the accuracy, efficiency, and the like of particle analysis and the like can be improved. For example, while an image analysis such as imaging that involves counting particles such as cells on the basis of the particle shape may produce a false positive result if a bubble equal to particles such as cells in size is entrained, the present technology can reduce, prevent, or avoid producing such result because of the capability to discharge entrained bubbles. For example, in a case where particles such as cells are trapped and an image is obtained by imaging the particles such as cells that have been trapped, as compared with the case where bubbles are entrained, the present technology provides a better contrast because the present technology provides the capability to discharge entrained bubbles.

Note that effects provided by the present technology are not necessarily limited to the effects described above, but may be any of the effects described herein.

2-5. Example 1 of Apparatus According to the Present Technology

An example of the apparatus according to the present technology is shown below (see FIGS. 2, 6A, 6B, 6C, 6D, 6E, and 7, for example), but the present technology is not limited thereto.

The apparatus of the present technology is provided with a chamber 100 that includes a microchip that includes at least one well 2 to divide a space into a first space 3 and a second space 4. The chamber 100 preferably includes a pressure control unit 20. The well 2 may be provided with a hole 8 in a well bottom 7, or the well 2 may be a through hole, and it is preferable that the well 2 or the through hole is connected to the first space 3 and the second space 4. The well 2 or the through hole preferably has a size (or a space) that allows only one particle to enter the well 2 or the through hole. Furthermore, the chamber 100 preferably has a region 9 (hereinafter also referred to as "a well/through hole region 9") that includes at least one well 2 or through hole.

The space in the chamber 100 of the present technology is divided into the first space 3 and the second space 4 by the well/through hole region 9.

The first space 3 is connected to first flow paths 5, 5. It is preferable that either one and the other one of the first flow paths 5, 5 are connected to a first supply valve 51 and a first discharge valve 52, respectively. Opening/closing operations of the first valves 51, 52 connected to the first flow path 5 can control supply and discharge of a fluid to the first space 3. For convenience, the first supply valve 51 is used as a supply valve and the first discharge valve 52 is used as a discharge valve, but the first valves 51 and 52 can be interchanged for supply or discharge as appropriate.

The second space 4 is connected to second flow paths 6, 6. It is preferable that either one and the other one of the second flow paths 6, 6 are connected to a second supply valve 61 and a second discharge valve 62, respectively. Opening/closing operations of the second valves 61, 62 connected to the second flow path 6 can control supply and discharge of a fluid to the second space 4. For convenience, the second supply valve 61 is used as a supply valve and the second discharge valve 62 is used as a discharge valve, but the second valves 61 and 62 can be interchanged for supply or discharge as appropriate.

In addition, the first flow path 5 may be connected, vie the first supply valve 51 or the first discharge valve 52, to a flow path for supplying a fluid and/or to a flow path for discharging a fluid.

Furthermore, the second flow path 6 may be connected, vie the second supply valve 61 or the second discharge valve 62, to a flow path for supplying a fluid and/or to a flow path for discharging a fluid.

Furthermore, the flow path for supplying a fluid and/or the flow path for discharging a fluid may be connected to the first space 3 or the second space 4 via the first flow path 5 or the second flow path 6, or may be directly connected to the first space 3 or the second space 4. The fluid may contain particles.

The pressure control unit 20 is configured to discharge bubbles in the chamber 100, which includes a microchip that includes at least one well 2 or through hole to divide a space into the first space 3 and the second space 4. The pressure control unit 20 is configured to exert control for discharging bubbles in the chamber by performing a pressurizing step of applying a positive pressure to a fluid in the chamber and a valve opening/closing step of operating valves 51, 52, 61, and 62 for opening/closing the first flow path 5 connected to the first space 3 and the second flow path 6 connected to the second space 4. In addition, the pressure control unit 20 makes it possible to carry out the method described in <1. Bubble discharging method according to the present technology> above, and the apparatus of the present technology is configured to carry out the bubble discharging method of the present technology.

Furthermore, it is preferable that the apparatus of the present technology is capable of trapping particles in the chamber. In this case, the well/through hole region 9 functions as a particle trapping region for trapping particles, and particles can be trapped in the well 2 or the through hole. Furthermore, the apparatus of the present technology is preferably a particle trapping apparatus or a particle analyzing apparatus.

It is preferable that the apparatus of the present technology includes a suction unit (not illustrated) that draws a fluid or a fluid containing particles present in the first space 3 or the second space 4. The suction unit can be directly or indirectly connected to the first space 3 and/or the second space 4. In a case where the suction unit is indirectly connected to the first space 3 or the second space 4, the suction unit may be connected thereto via, for example, the first flow path 5 and/or the second flow path 6.

The suction unit makes it possible to draw the particles to the side opposite to the side on which the particles settle and, furthermore, to adjust the speed of sedimentation of the particles.

The chamber 100 of the present technology may be configured to be capable of observing the particles trapped in the well 2 using an imaging apparatus (not illustrated) such as a microscope 80. For example, the chamber preferably includes a transparent material so that one side of the chamber can be observed. Thus, if at least part of the chamber includes a transparent material, the trapped particles can be observed by an observation unit such as the microscope 80 (for example, an upright microscope, an inverted microscope, or the like), for example. The well 2 or through hole, a particle S, a bubble, and the like present in the flow path can be observed from the upper surface or the lower surface of the well/through hole region 9 of the chamber by the observation unit such as the microscope 80.

In addition, the observation unit may further include an imaging apparatus (not illustrated). Examples of the imaging apparatus may include an imaging apparatus equipped with an image sensor, particularly a digital camera, for example. The image sensor may be, for example, a charge coupled device (CCD) or a complementary metal oxide semiconductor (CMOS). Image data obtained by imaging may be stored in the imaging apparatus or the analysis unit, or may be stored in an external data storage apparatus connected to the imaging apparatus in a wired or wireless manner.

In the present technology, bubbles present in a fluid in the chamber can be efficiently discharged. As a result, the accuracy, the efficiency, and the like of particle analysis, particle trapping, and the like can be improved in an apparatus or system that employs a flow path system for assaying, trapping, analyzing, and the like of particles. Note that effects provided by the present technology are not necessarily limited to the effects described above, but may be any of the effects described herein.

Note that the particles trapped in the well may be subjected to various observations and/or measurements. For example, a predetermined fluorescent label may be attached to particles before the particles are supplied into the chamber, and the particle that emits the strongest fluorescence after trapped may be selected from the trapped particles. Furthermore, only the selected particle can be taken out of the particle trapping chamber by, for example, a single particle taking apparatus such as a micromanipulator. Then, a still another process is performed by using the selected particle. In a case where the particles are cells, such another process may be, for example, gene analysis, culture, substance production, and the like.

Furthermore, for example, it is possible to select particles having desired characteristics, such as selection of cells that secrete desired antibodies, selection of cells or microorganisms that express desired genes, and selection of cells that have desired differentiation potential.

2-6. Example 2 of Apparatus According to the Present Technology

Figure 9:
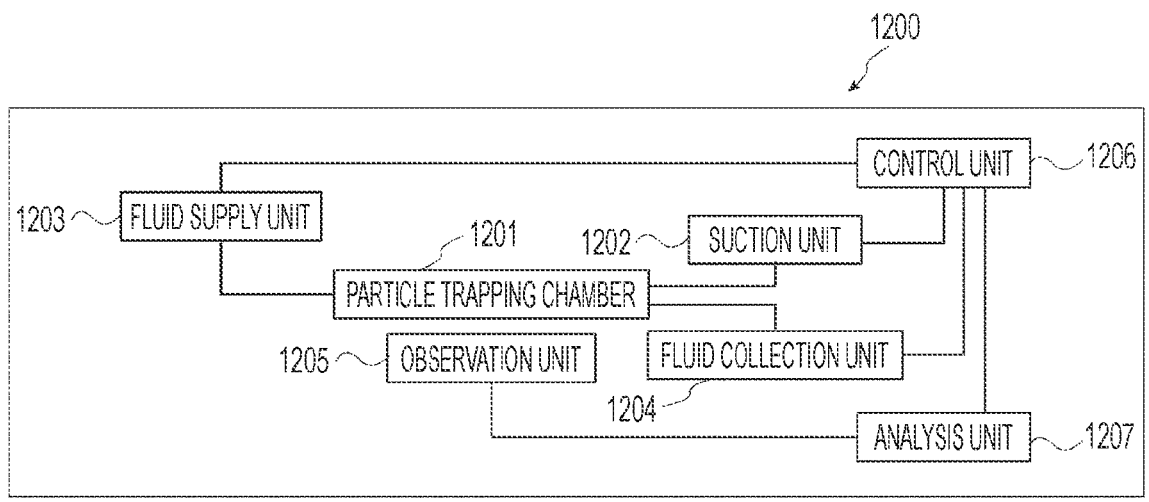
FIG. 9 is a block diagram of an example of the apparatus of the present technology.

The following describes Example 2 of another aspect of the apparatus according to the present technology with reference to FIG. 9. FIG. 9 is a block diagram of an example of the apparatus of the present technology.

As illustrated in FIG. 9, an apparatus 1200 of the present technology includes a particle trapping chamber 1201, a suction unit 1202, a fluid supply unit 1203, a fluid collection unit 1204, an observation unit 1205, a control unit 1206, and an analysis unit 1207, and the control unit 1206 includes a pressure control unit (not illustrated). Note that the apparatus of the present technology is not limited thereto.

The particle trapping chamber 1201 includes a particle trapping region and a particle trapping flow path unit, the particle trapping region including at least one well or through hole, and the particle trapping flow path unit being used to trap a particle into the well or into the through hole. The particle trapping chamber 1201 further includes a fluid supply flow path unit and a fluid discharge flow path unit.

In the present technology, the particle trapping region may be replaceable. The particle trapping chip in the particle trapping chamber 1201 may be disposed detachably from the chamber. Then, the particle trapping chip may be replaced with a new one by a user at every analysis or the like.

Alternatively, the particle trapping chamber 1201 itself may be replaceable. That is, the particle trapping chamber 1201 may be detachably disposed in the apparatus 1200 according to the present technology. For example, according to the present technology, a cartridge-like particle trapping chamber unit in which the particle trapping chip is integrated with a chip holder holding the chip may be replaceably disposed in the apparatus 1200 according to the present technology. In this case, the user can change the particle trapping regions by changing the cartridges, which is easier than replacing the particle trapping region itself that is formed into a small-sized thin film. Furthermore, in this case, the well can be kept free from dust because the chamber is not exposed.

The suction unit 1202 is capable of drawing particles in the chamber via the first flow path and the second flow path in the particle trapping chamber 1201. For example, the suction unit provides suction in the above-described particle trapping step. The suction unit 1202 may be connected to the particle trapping chamber 1201 (for example, the first space and second space, the first flow path and second flow path, and the like) so as to provide the suction. In this connection, for example, a tube for suction may communicate with the chamber. A valve may be disposed on the tube. The suction unit includes, for example, a pump.

The fluid supply unit 1203 supplies a fluid containing particles to the particle trapping chamber 1201. For example, in the particle trapping step described above, the fluid supply unit 1203 is used to supply a fluid containing particles into the particle trapping chamber by supply or suction. The fluid supply unit includes, for example, a container capable of storing a fluid containing particles and a tube connected to the container. The tube may communicate with the particle trapping chamber 1201 (for example, the first space and second space, and the first flow path and second flow path). A valve may be disposed on the tube.

The fluid collection unit 1204 collects a fluid from the particle trapping chamber 1201. For example, the fluid collection unit 1204 removes particles in the removal step described above. The fluid collection unit 1204 may be connected to the particle trapping chamber 1201 so that a fluid can be collected from the particle trapping chamber 1201. For example, the particle trapping chamber 1201 (for example, the first space and second space, the first flow path and second flow path, and the like) may communicate with a tube for collecting a fluid in the fluid collection unit 1204. A valve may be disposed on the tube. The fluid collection unit 1204 may include, for example, a pump. A fluid in the chamber is collected by suction provided by the pump. The fluid collection unit 1204 may be connected to the particle trapping chamber 1201 via, for example, a liquid collection container so that the liquid drawn by the fluid collection unit is prevented from entering the pump.

The number of fluid collection units 1204 that may be disposed in the particle trapping chamber 1201 is one, two, or three or more. For example, in a case where two fluid collection units are included in the particle trapping chamber 1201, one of the fluid collection units may be used to collect the particles that were not trapped into the well or through hole, and the other one of the fluid collection units may be used to collect the particles that were trapped into the well or through hole.

The observation unit 1205 is used to observe the particles trapped in the well or through hole and/or to understand characteristics of the particles trapped in the well or through hole. In addition, the observation unit 1205 may be used to identify bubbles entrained in the chamber.

Furthermore, observation of a particle may include, for example, observing the shape, structure, color, and/or the like of the particle itself. Understanding characteristics of a particle may include, for example, identifying the wavelength and/or the intensity of light emitted from the particle such as fluorescence or the like.

Furthermore, observation of entrained bubbles may include, for example, observing the size of a bubble itself and the number of bubbles, the movement of bubbles, and the like. Entrained bubbles may be observed by focusing on a bubble or imaging a bubble. In addition, the observation of bubbles may include capturing an image after bubbles are imaged and understanding the bubbles such as analyzing the size of a bubble, the number of bubbles, and movement of bubbles in the image.

The observation unit 1205 may be, for example, an apparatus that achieves the observation and/or the understanding, and may be, for example, a microscope and/or a photodetector. In the case of observing bubbles, a microscope is preferably used for the observation. The particle observation and the bubble observation may be made by providing separate apparatus, or may be made with the same apparatus.

In the present technology, the observation unit 1205 is disposed at a position that allows bubbles or particles in the chamber to be observed. For example, the observation unit 1205 may be disposed above and/or under the particle trapping chamber 1201. For example, it is preferable to use an inverted microscope as the microscope. Furthermore, the microscope may be preferably an optical microscope. In other words, in the present technology, the observation unit 1205 preferably includes an inverted optical microscope.

In order to observe the appearance characteristics of cells, a generally employed bright-field observation or dark-field observation may be employed in the present technology. In addition, when a cell is observed in the state where the fine internal structure of a transparent cell is emphasized, the phase contrast observation or differential interference observation suitable for such case may be employed in the present technology. Employing any of these observation techniques makes it possible to observe live cells without staining the cells. To observe transparent cells, it is particularly preferable to employ phase contrast observation. In a case where phase contrast observation is employed, the observation unit 1205 preferably includes a halogen lamp light source, an objective lens, a phase plate, a condenser lens, and a ring aperture.

Furthermore, if a cell is labeled with a fluorescent protein, the cell can be observed by fluorescence observation in the state where a specific portion of interest in the cell is emphasized. Such fluorescence observation is used in various applications such as, for example, identification of an antigen in an antigen-antibody reaction or visualization of intracellular structures such as mitochondria. For fluorescence observation, the observation unit 1205 preferably includes an excitation light source (usually a mercury lamp), a filter for selecting the wavelength of excitation light, a dichroic mirror for extracting the fluorescence having the wavelength of light emitted by a substance, and an absorption filter for cutting off wavelengths other than the fluorescence wavelength. Selecting a combination of an excitation wavelength and a fluorescence wavelength through a filter makes it possible to conduct various analyses on a single observation image.

In addition, the observation unit 1205 may further include an imaging apparatus. Examples of the imaging apparatus may include an imaging apparatus equipped with an image sensor, particularly a digital camera, for example. The image sensor may be, for example, a charge coupled device (CCD) or a complementary metal oxide semiconductor (CMOS). Image data obtained by imaging may be stored in the imaging apparatus or the analysis unit 1207, or may be stored in an external data storage apparatus connected to the imaging apparatus in a wired or wireless manner.

The control unit 1206 may control the suction unit 1202, the fluid supply unit 1203, and/or the fluid collection unit 1204. For example, the control unit 1206 may control pumps and/or valves for the suction unit 1202, the fluid supply unit 1203, and/or the fluid collection unit 1204. As a result, various steps or the like in the particle trapping method or the particle analyzing method of the present technology may be performed.

Furthermore, the control unit 1206 may control the pressure control unit or include the pressure control unit inside or outside the control unit 1206. As a result, various steps in the bubble discharging step of the present technology, such as the pressurizing step, the valve opening/closing step, the bubble analyzing step, may be performed, and the like.

The analysis unit 1207 analyzes the data obtained by the observation unit 1205, such as image data, data relating to light, or the like. For example, the analysis unit 1207 can conduct analysis in the analyzing step in the bubble discharging method described above or in the analyzing step in the particle trapping method or the particle analyzing method.

The analysis unit 1207 can select, for example, a particle or entrained bubble having a predetermined shape or color on the basis of the obtained image data. Alternatively, in the case of particles, the analysis unit 1207 can select a particle that emits predetermined fluorescence on the basis of the obtained data relating to light. The position information regarding the selected particle or entrained bubble may be transmitted from the analysis unit 1207 to an apparatus of the present technology connected thereto in a wired or wireless manner, such as a single particle trapping apparatus (for example, a micromanipulator or the like) or the like. On the basis of the position information regarding the entrained bubble, the movement, size, number, and the like of entrained bubbles may be understood and used for discharging bubbles. Furthermore, on the basis of the position information regarding the particle, the selected particle may be independently acquired by the single particle trapping apparatus.

In addition to the components described above, the apparatus 1200 may include any other component such as the above-mentioned single particle trapping apparatus or the like. Furthermore, the apparatus 1200 may include, as necessary, a storage unit that stores various types of data, an input unit for inputting instructions from the user regarding entrained bubbles or particle trapping, an output unit that outputs various results such as a result of observation or analysis of entrained bubbles, a result of trapping, a result of analysis, and the like.

Note that the present technology may have the following configurations.

[1]

A bubble discharging method carried out in a chamber including a microchip that includes at least one well or through hole to divide a space into a first space and a second space, the bubble discharging method including:

a pressurizing step of applying a positive pressure to a fluid in the chamber; and a valve opening/closing step of operating a valve for opening/closing a first flow path connected to the first space and/or a second flow path connected to the second space.

[2]

The bubble discharging method according to [1], in which the microchip includes a particle trapping chip that includes a particle trapping region including at least one well or through hole.

[3]

The bubble discharging method according to [1] or [2], in which
the first flow path includes a flow path that is connected to a first supply valve from which a fluid is supplied and to a first discharge valve from which the fluid is discharged, and/or
the second flow path includes a flow path that is connected to a second supply valve from which the fluid is supplied and to a second discharge valve from which the fluid is discharged.

[4]

The bubble discharging method according to [3], in which the valve opening/closing step includes a step of opening/closing the supply valve and/or the discharge valve after a positive pressure is applied to the fluid in the chamber and discharging a bubble from the chamber.

[5]

The bubble discharging method according to any one of [1] to [4], in which
the pressurizing step and the valve opening/closing step are repeatedly performed.

[6]

The bubble discharging method according to any one of [1] to [5], further including:
a bubble analyzing step of analyzing a bubble in the chamber on the basis of information acquired by imaging the bubble in the chamber.

[7]

The bubble discharging method according to [6], in which in the bubble analyzing step, it is determined whether or not a bubble in the chamber meets a predetermined condition, and, if it is determined that the bubble meets the predetermined condition, the pressurizing step and the valve opening/closing step are performed.

[8]

The bubble discharging method according to any one of [2] to [7], in which
in the pressurizing step, the fluid in the chamber is pressurized in a state where the supply valve is opened and valves other than the supply valve are closed, and
in the valve opening/closing step, after the supply valve is closed, at least any one of the closed valves is intermittently opened.

[9]

The bubble discharging method according to any one of [2] to [7], in which
in the pressurizing step, the fluid in the chamber is pressurized in a state where the supply valve is opened and valves other than the supply valve are closed, and
in the valve opening/closing step, at least any one of the closed valves is opened.

[10]

The bubble discharging method according to [2], in which the particle includes a single cell.

[11]

A particle trapping apparatus including:
a pressure control unit that performs control, in a chamber including a microchip that includes at least one well or through hole to divide a space into a first space and a second space,
so as to perform a pressurizing step of applying a positive pressure to a fluid in the chamber and
a valve opening/closing step of operating a valve for opening/closing a first flow path connected to the first space and/or a second flow path connected to the second space, and to discharge a bubble in the chamber, in which
the particle trapping apparatus traps a particle into the well or the through hole.

[12]

The particle trapping apparatus according to [11], in which
the microchip is disposed in such a way that an upper side of the first space is gradually higher in a discharge direction.

[13]

The particle trapping apparatus according to [12], in which
the microchip is disposed in such a way that a cross-sectional area of the microchip across a width direction is gradually larger in the discharge direction.

[14]

The particle trapping apparatus according to any one of [11] to [13], in which
the pressure control unit carries out the bubble discharging method according to any one of [3] to [9].

[15]

A particle analyzing apparatus including:
a pressure control unit that performs control, in a chamber including a microchip that includes at least one well or through hole to divide a space into a first space and a second space,
so as to perform a pressurizing step of applying a positive pressure to a fluid in the chamber and
a valve opening/closing step of operating a valve for opening/closing a first flow path connected to the first space and/or a second flow path connected to the second space, and to discharge a bubble in the chamber;
an observation unit that images, with a microscope, a bubble in the chamber and/or a particle trapped in the well or the through hole; and
an analysis unit that conducts an analysis relating to the bubble and/or the particle trapped on the basis of information acquired from the observation unit.

[16]

The particle trapping apparatus according to any one of [15], in which
the pressure control unit and the observation unit are controlled by a central control unit, and the central control unit carries out the bubble discharging method according to any one of [3] to [9].

REFERENCE SIGNS LIST

2 Well
3 First space
4 Second space
5 First flow path
6 Second flow path
7 Well bottom
8 Hole
9 Well/through hole region
10 Microchip 20 Pressure controller, pressure control unit
51 First supply valve
52 First discharge valve
61 Second supply valve
62 Second discharge valve
P Pump
70 Container
71 Particle flow path
72 Particle supply valve
80 Microscope, inverted microscope
100 Chamber
1200 Apparatus
1201 Particle trapping chamber
1202 Suction unit
1203 Fluid supply unit
1204 Fluid collection unit
1205 Observation unit
1206 Control unit

The invention claimed is:

1. A bubble discharging method carried out in a chamber including a microchip that includes at least one well or through hole to divide a space into a first space and a second space, the bubble discharging method comprising:
applying a positive pressure greater than a threshold to a fluid in the chamber based on presence of a bubble in the chamber;
opening a first flow path connected to the first space or a second flow path connected to the second space based on the application of the positive pressure greater than the threshold;
discharging the bubble from the chamber based on the application of the positive pressure greater than the threshold, and the opening of the first flow path or the second flow path; and
closing the first flow path or the second flow path based on the discharge of the bubble from the chamber, wherein
based on a determination that the first flow path is opened, the first flow path is closed, and
based on a determination that the second flow path is opened, the second flow path is closed.

2. The bubble discharging method according to claim 1, wherein
the microchip comprises a particle trapping chip that includes a particle trapping region including at least one well or through hole.

3. The bubble discharging method according to claim 1, wherein
the first flow path includes a flow path that is connected to a first supply valve from which the fluid is supplied and to a first discharge valve from which the fluid is discharged,
the second flow path includes a flow path that is connected to a second supply valve from which the fluid is supplied and to a second discharge valve from which the fluid is discharged, and
a plurality of valves includes the first supply valve, the first discharge valve, the second supply valve, and the second discharge valve.

4. The bubble discharging method according to claim 3, further comprises
opening of the first supply valve or the second supply valve, and the first discharge valve or the second discharge valve after the positive pressure greater than the threshold is applied to the fluid in the chamber; and
closing of the first supply valve or the second supply valve and the first discharge valve or the second discharge valve after the discharge of the bubble from the chamber.

5. The bubble discharging method according to claim 4, wherein
the application of the positive pressure greater than the threshold, and the opening or closing of each of the plurality of valves are repeatedly executed.

6. The bubble discharging method according to claim 5, further comprising:
analyzing the bubble in the chamber based on information acquired by imaging the bubble in the chamber, wherein
the analysis of the bubble is repeatedly executed after the application of the positive pressure greater than the threshold, and the opening or closing of each of the plurality of valves based on the repeated execution of the application of the positive pressure greater than the threshold, and the opening or closing of each of the plurality of valves.

7. The bubble discharging method according to claim 6, further comprises
executing, based on a determination that the bubble in the chamber meets a specific condition, the application of the positive pressure greater than the threshold, and the opening or closing of each of the plurality of valves.

8. The bubble discharging method according to claim 3, wherein
the fluid in the chamber is pressurized based on a determination that the first supply valve is opened and the plurality of valves excluding the first supply valve are closed, and
based on a determination that the first supply valve is closed, at least one valve of the first discharge valve or the second discharge valve is intermittently opened.

9. The bubble discharging method according to claim 3, wherein
the fluid in the chamber is pressurized based on a determination that the first supply valve is opened and the plurality of valves excluding the first supply valve are closed, and
after the pressurization, at least one valve of the first discharge valve or the second discharge valve is opened along with the opened the first supply valve.

10. The bubble discharging method according to claim 2, wherein
the particle trapping region includes a particle, and the particle comprises a single cell.

11. A particle trapping apparatus, comprising:
a pressure control unit configured to:
control, in a chamber including a microchip that includes at least one well or through hole to divide a space into a first space and a second space, application a positive pressure to a fluid in the chamber;
control opening of a valve for opening a first flow path connected to the first space and a second flow path connected to the second space based on the application of the positive pressure greater than a threshold;
discharge a bubble in the chamber based on the application of the positive pressure and the opening of the valve, wherein the particle trapping apparatus is further configured to trap a particle into the well or the through hole; and
control closing of the valve for closing the first flow path connected to the first space and the second flow path connected to the second space based on the discharge of the bubble in the chamber.

12. The particle trapping apparatus according to claim 11, wherein
the microchip is in such a way that an upper side of the first space is gradually higher in a discharge direction.

13. The particle trapping apparatus according to claim 12, wherein
the microchip is in such a way that a width direction of the microchip is gradually larger in the discharge direction.

14. A particle analyzing apparatus, comprising:
a pressure control unit configured to:
control, in a chamber including a microchip that includes at least one well or through hole to divide a space into a first space and a second space, application of a positive pressure to a fluid in the chamber;
control opening of a valve for opening a first flow path connected to the first space and a second flow path connected to the second space based on the application of the positive pressure greater than a threshold;
discharge a bubble in the chamber based on the application of the positive pressure and the opening of the valve; and
control closing of the valve for closing the first flow path connected to the first space and the second flow path connected to the second space based on the discharge of the bubble in the chamber;

an observation unit configured to image, with a microscope, a bubble in the chamber or a particle trapped in the well or the through hole; and an analysis unit configured to conduct an analysis relating to the bubble or the particle trapped based on information acquired from the observation unit.

* * * * *